US009512483B2

(12) United States Patent
Belinsky

(10) Patent No.: US 9,512,483 B2
(45) Date of Patent: Dec. 6, 2016

(54) GENE METHYLATION AS A BIOMARKER IN SPUTUM

(75) Inventor: Steven A. Belinsky, Albuquerque, NM (US)

(73) Assignee: LOVELACE RESPIRATORY RESEARCH INSTITUTE, Albuquerque, NM (US)

( * ) Notice: Subject to any disclaimer, the term of this patent is extended or adjusted under 35 U.S.C. 154(b) by 1197 days.

(21) Appl. No.: 11/995,150

(22) PCT Filed: Jul. 10, 2006

(86) PCT No.: PCT/US2006/026571
§ 371 (c)(1),
(2), (4) Date: Jan. 9, 2008

(87) PCT Pub. No.: WO2007/008693
PCT Pub. Date: Jan. 18, 2007

(65) Prior Publication Data
US 2008/0241842 A1 Oct. 2, 2008

Related U.S. Application Data

(60) Provisional application No. 60/698,208, filed on Jul. 9, 2005.

(51) Int. Cl.
*C12Q 1/68* (2006.01)
*C07H 21/04* (2006.01)

(52) U.S. Cl.
CPC ........ *C12Q 1/6886* (2013.01); *C12Q 2523/125* (2013.01); *C12Q 2600/154* (2013.01); *C12Q 2600/16* (2013.01)

(58) Field of Classification Search
CPC ............ C12Q 1/6886; C12Q 2537/164; C12Q 2600/154; C12Q 2537/16; C12Q 1/6883; C12Q 2600/158; C12Q 2521/331; C12Q 2600/112; G01N 33/574
See application file for complete search history.

(56) References Cited

U.S. PATENT DOCUMENTS

| 5,487,972 | A * | 1/1996 | Gelfand et al. ............. 536/23.1 |
| 5,541,308 | A | 7/1996 | Hogan et al. |
| 2003/0138780 | A1* | 7/2003 | Gill et al. .......................... 435/6 |
| 2003/0219760 | A1* | 11/2003 | Gordon et al. .................... 435/6 |
| 2004/0038245 | A1 | 2/2004 | Belinsky et al. |
| 2005/0026183 | A1 | 2/2005 | Fan et al. |
| 2005/0037354 | A1 | 2/2005 | Berlin et al. |

FOREIGN PATENT DOCUMENTS

WO WO 0218649 A1 * 3/2002
WO WO 03064682 A1 * 8/2003

OTHER PUBLICATIONS

Kikuchi et al. (Clin Cancer Research Apr. 15, 2005 vol. 11 p. 2954).*
Akiyama et al. (Molecular and cellular biology Dec. 2003 vol. 23 p. 8429).*
Guo (Clinical Cancer Research 2004 vol. 10 p. 7917).*
Akiyama, Yoshimitsu et al., "GATA-4 and GATA-5 Transcription Factor Genes and Potential Downstream Antitumor Target Genes are Epigenetically Silenced in Colorectal and Gastric Cancer", *Molecular and Cellular Biology* vol. 23, No. 23, American Society for Microbiology Dec. 2003 , 8429-8439.
Belinsky, Steven A. et al., "Aberrant Promoter Methylation in Bronchial Epitheliujm and Sputum from Current and Former Smokers", *Cancer Research* vol. 62 Apr. 15, 2002 , 2370-2377.
Hesson, L. B. et al., "CpG island promoter hypermethylation of a novel Ras-effector gene RASSF2A in an early event in colon carcinogenesis and correlates inversely with K-ras mutation", *Oncogene* vol. 24, http://www.nature.com/onc/journal/v24/n24/abs/1208566a.html Apr. 4, 2005 , 8429-8439.
Kikuchi, Shinji et al., "Promoter Methylation of DAL-1/4.1B Predicts Poor Prognosis in Non-Small Cell Lung Cancer", *Clin Cancer Res* vol. 11, No. 8, www.aacrjournals.org Apr. 15, 2005 , 2954-2961.
Palmisano, William A. et al., "Aberrant Promoter Methylation of the Transcription Factor Genes PAX5 Alpha and Beta in Human Cancers", *Cancer Research* vol. 63 Aug. 1, 2003 , 4620-4625.
Palmisano, William A. et al., "Predicting Lung Cancer by Detecting Aberrant Promoter Methylation in Sputum", *Cancer Research* vol. 60 Nov. 1, 2001 , 5954-5958.
Prindiville, Sheila A. et al., "Sputum Cytological Atypia as a Predictor of Incident Lung Cancer in a Cohort of Heacy Smokers with Airflow Obstruction", *Cancer Epidemiology, Biomarkers & Prevention* vol. 12 Oct. 2003 , 987-993.
Herman, James G. et al., "Methylation-specific PCR: A novel PCR assay for methylation status of CpG Islands", Proc. Natl. Acad. Sci., vol. 93, Sep. 1996, 9821-9826, Aug. 15, 2011.

* cited by examiner

*Primary Examiner* — Katherine Salmon
(74) *Attorney, Agent, or Firm* — Janeen C. Vilven-Doggett; Peacock Myers, P.C.

(57) ABSTRACT

The present invention provides for a method to monitor the health of a subject. The method includes obtaining a test sample from the patient. A first probe specific for a CpG promoter region of a biomarker selected from p16, MGMT, PAX-α, PAX5-β, RASSF1A, HLHP, GATA4, GATA5, SFRP1, LAMC2, IGFBP3, H-cadherin, BETA 3, HLHP, and DAPK is provided to the sample. The probe contacts the test sample. The DNA of interest from the test sample is isolated. A second stage probe specific for a second CpG promoter region of a biomarker selected from p16, MGMT, PAX-α, PAX5-β, RASSF1A, HLHP, GATA4, GATA5, SFRP1, LAMC2, IGFBP3, H-cadherin, BETA 3, HLHP, and DAPK is provided to the sample to form a second stage PCR product. The DNA is analyzed for hypermethylation of the promoter region for at least one of p16, MGMT, PAX-α, PAX5-β, RASSF1A, HLHP, GATA4, GATA5, SFRP1, LAMC2, IGFBP3, H-cadherin, BETA 3, HLHP, and DAPK. Hypermethylation of the promoter region of at least one of p16, MGMT, PAX-α, PAX5-β, RASSF1A, HLHP, GATA4, GATA5, SFRP1, LAMC2, IGFBP3, H-cadherin, BETA 3, HLHP, and DAPK is an indication that the subject is at increased risk of developing cancer for example, non small cell lung cancer.

14 Claims, 3 Drawing Sheets

GENE METHYLATION AS A BIOMARKER IN SPUTUM

The present invention relates to methods for monitoring one or more genes that are down-regulated in cells or tissues having disease including lung cancer. Lung cancer is the leading cause of cancer mortality in the United States and 1.5 million deaths are projected worldwide from this disease by 2010. The overall five-year survival rate for lung cancer is <15% due largely to the late stage at which most patients are diagnosed and the lack of effective treatments for systemic disease. A validated screening approach for lung cancer could substantially reduce the high mortality rate for this disease. The benefit of early detection is seen in patients with stage I tumors (<3 cm) where surgical resection is commonly the preferred treatment option, and the rate of recurrence within 5 years is <50%. With the adoption of adjuvant chemotherapy for these early stage lung cancer patients, the rate of recurrence should decline further.

Cytologic and/or genetic biomarkers for lung cancer risk detected in sputum could complement radiological imaging and bronchoscopy for detecting early lung tumors. Previous studies have shown that cytological atypia present in epithelial cells exfoliated into sputum precedes lung cancer diagnosis. However, cytological screening is subjective and hard to replicate.

Transcriptional silencing of genes by CpG island methylation is recognized as a component in lung cancer initiation and progression. The development of the methylation specific PCR (MSP) assay has allowed for the assay of methylation of specific genes in serum at a level of 1 in 1000. However, this level of sensitivity is inadequate to be useful in screening for early stage cancers since the methylated transcripts of the gene of interest are only present in a sample in a mixed ratio with unmethylated transcripts. Therefore, improving sensitivity limits is required to provide early detection screening for lung cancer using genetic biomarkers.

The well-documented field cancerization seen in lungs from smokers, stemming from the exposure of the entire respiratory tract to inhaled carcinogens within cigarette smoke, presents an obstacle to the early detection of lung cancer. The generation of multiple, independently initiated sites throughout the lungs of people with a long history of smoking likely accounts for detecting methylation of genes such as p16 that is inactivated in the earliest stages of preinvasive disease. The use of promoter methylation as a biomarker for early detection of lung cancer whose presence in sputum confer a high enough sensitivity and specificity for distinguishing very advanced dysplasia or early lung cancer from the large "at risk" population is desired. The development of a validated screening approach for lung cancer could markedly reduce the high mortality rate for this disease.

BRIEF SUMMARY

One aspect of the present invention provides for a method of screening samples from a subject for early stage cancer detection. The samples can be for example, sputum, blood or urine but are not limited thereto. For example, screening the promoter CpG methylation condition of a validated panel of genes is useful as a predictive indicator of health, particularly lung health. The sites within the CpG islands of one or more genes are useful for screening for the health of the subject and as an indicator of the likelihood of developing cancer, particularly lung cancer. Additionally, a quantitative analysis of the biomoarker panel aids in assigning an index value correlated to the health of the subject; and future health of the subject as well as assessing or monitoring of therapy or recovery from a disease such as cancer.

Another aspect of the present invention provides for a method of monitoring the efficacy of a cancer therapy.

Yet another aspect of the present invention provides for a panel of first stage primers that increase sensitivity of detection for a panel of biomarkers that are an indicator of a subject's health.

Yet another aspect of the present invention provides for a panel of first stage primers that increase sensitivity of detection for a panel of biomarkers that are indicative of a subject's health, predictive of cancer or a combination thereof.

Still another aspect of the present invention provides for a panel of second stage primers that increase sensitivity of detection for a panel of biomarkers that are predictive of cancer.

Another aspect of the present invention provides for a kit useful in the monitoring of the health of a subject.

One embodiment of the present invention provides a method to monitor the health of a subject comprising obtaining a test sample from the subject containing DNA. The test sample is a biological sample for example from tissue plasma, ejaculate, cerebrospinal fluid, serum, mammary duct fluid, urine, and fecal stool and sputum. The test sample may contain one or more cells, and the cells may contain at least one specific gene that is the gene that is altered by the cancer in the cell.

The DNA in the test sample is subjected to bisulfite modification. A first primer set specific for a first CpG promoter region of a gene selected from p16, MGMT, DAPK, PAX5-alpha, PAX-beta, RASSF1A, DAB-2, DAL-1, RASSF2A, GATA5, and GATA4 is provided to the sample. The number of copies of the portion of the gene where the promoter CpG islands reside and to which the primer is annealed is expanded by using a polymerase chain reaction, thereby generating an amplification product. An aliquot of the amplification product generated by the first polymerase chain reaction is used in a second, methylation-specific, polymerase chain reaction using a second primer set specific for at least one of the gene portions previously amplified at a temperature of annealing that exceeds the melting temperature of a second primer set, to detect the presence of inactivation of the at least one specific gene. The product of the first and second stage PCR steps is analyzed for hypermethylation of the promoter region of at least one of p16, MGMT, DAPK, PAX5-alpha, PAX-beta, RASSF1A, DAB-2, DAL-1, RASSF2A, GATA5, and GATA4.

According to another embodiment, an index value associated with the health of the subject is determined from the total number of genes with hypermethylation in the promoter region using an algorithm.

One embodiment of the present invention provides that hypermethylation of the promoter region of one or more of the following genes p16, MGMT, DAPK, PAX5-alpha, PAX-beta, RASSF1A, DAB-2, DAL-1, RASSF2A, and GATA5, GATA4, is an indication that the subject is at increased risk of developing cancer. Still another embodiment of the present invention provides a kit useful for the diagnosis, prognosis, monitoring and therapeutic treatment of a disease. The kit includes one or more primers that are very specific for detecting methylation of a CpG site in the promoter region of a gene selected from p16, MGMT, DAPK, PAX5-alpha, PAX-beta, RASSF1A, DAB-2, DAL-1, RASSF2A, GATA5, and GATA4, and a bisulflite reagent.

Yet another embodiment of the present invention provides a method to monitor the health of a subject. The method includes obtaining a test sample from the patient. A first primer specific for a CpG promoter region of at least one of p16, MGMT, DAPK, PAX5-alpha; PAX-beta, RASSF1A, DAB-2, DAL-1, RASSF2A, GATA5, and GATA4 is provided to the sample in a first polymerase chain reaction. The product of the first polymerase chain reaction is reacted with a second primer specific for a promoter region of at least one of p16, MGMT, DAPK, PAX5-alpha, PAX5-beta, RASSF1A, DAB-2, DAL-1, RASSF2A, GATA5, GATA4 wherein the annealing temperature of the second PCR is above the melting temperature of the second primer, for example, the temperature is elevated by about 4-10° C. Hypermethylation of one or more of the genes that are interrogated for their promoter methylation state indicate the health of the subject and an increased current risk and an increased future risk for developing cancer, for example lung cancer.

Another embodiment of the present invention provides that hypermethylation of the promoter region of any three (3) of a panel of genes comprising p16, MGMT, DAPK, PAX5-beta, RASSF1A, and GATA5, is an indication that the subject is at increased risk of developing cancer, particularly non small cell lung cancer.

Another embodiment of the present invention provides that hypermethylation of the promoter region of any three (3) of a panel of genes comprising p16, MGMT, DAPK, PAX5-alpha, PAX5-beta, RASSF1A, GATA5, and GATA4 is an indication that the subject is at increased risk of developing cancer, particularly lung cancer.

Another embodiment of the present invention provides that hypermethylation of the promoter region of any three (3) of a panel of genes comprising p16, MGMT, DAPK, PAX5-alpha, PAX5-beta, RASSF1A, DAB-2, DAL-1, RASSF2A, GATA5, and GATA4 is an indication that the subject is at increased risk of developing cancer, particularly lung cancer.

Another embodiment of the present invention provides that hypermethylation of the promoter region of one or more of DAB2, DAL-1, DAPK, PAX5-alpha, PAX5-beta, MGMT, P16, RASSF1A, RASSF2, GATA5, and GATA4A is an indication that the subject is at increased risk of developing cancer, particularly lung cancer.

Yet another embodiment of the present invention provides for a method of monitoring the efficacy of therapy for treating cancer, for example, lung cancer in a patient. The method includes obtaining a first test sample from the patient at a first time point. A first primer specific for the CpG promoter region of at least one of DAB2, DAL-1, DAPK, PAX5-alpha, PAX5-beta, MGMT, P16, RASSF1A, RASSF2, GATA5, and GATA4A is provided to the first test sample to expand the number of copies of the primer specific gene. A second primer set specific for the expanded gene is provided to the sample in a methylation-specific PCR reaction. DNA from the test sample is analyzed for hypermethylation of the promoter region for at least one of DAB2, DAL-1, DAPK, PAX5-alpha, PAX5-beta, MGMT, P16, RASSF1A, RASSF2A, GATA5, and GATA4A. A therapy for the treatment of lung cancer is provided to the patient. A second test sample is obtained from the patient at a second time point. A first primer specific for the CpG promoter region of at least one of DAB2, DAL-1, DAPK, PAX5-alpha, PAX5-beta, MGMT, P16, RASSF1A, RASSF2, GATA5, and GATA4A is provided to the second test sample to expand the number of copies of the primer specific gene. A second primer set specific for the expanded gene is provided to the sample in a methylation-specific PCR reaction. DNA from the second test sample is analyzed for hypermethylation of the promoter region for at least one of DAB2, DAL-1, DAPK, PAX5-alpha, PAX5-beta, MGMT, P16, RASSF1A, RASSF2, GATA5, and GATA4A whereby a decrease in the hypermethylation of the promoter region of at least one of DAB2, DAL-1, DAPK, PAX5-alpha, PAX5-beta, MGMT, P16, RASSF1A, RASSF2, GATA5, and GATA4A is an indication of the efficacy of the therapy.

DETAILED DESCRIPTION

Figure 1:
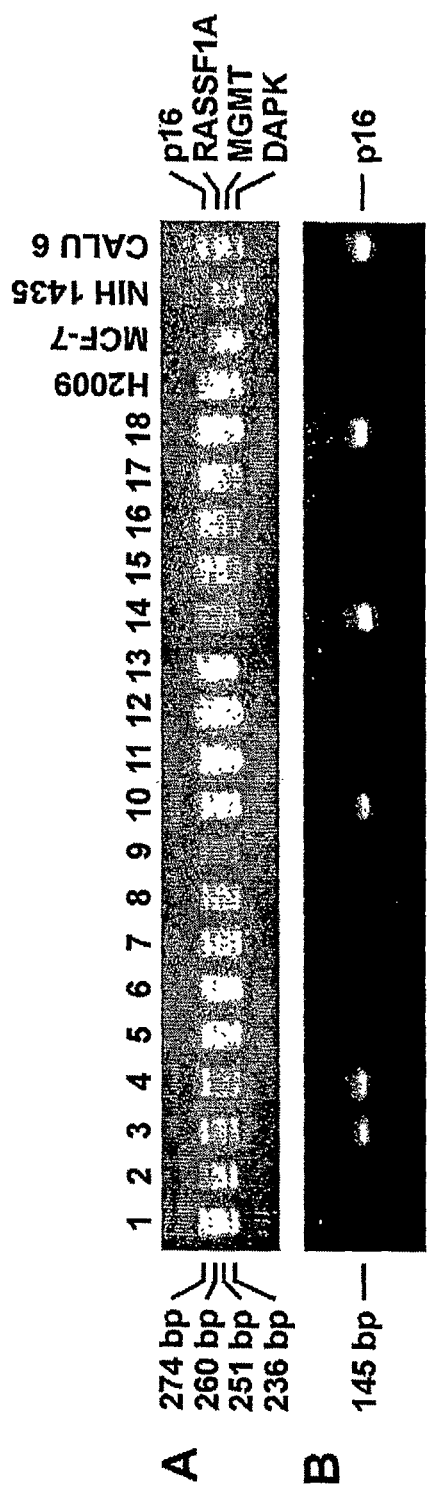
FIG. 1 illustrates products from a MSP amplification of the p16, MGMT, DAPK, and RASSF1A genes.

One aspect of the present invention is directed toward a method of screening individuals for genetic evidence that places the individual at an increased risk for developing cancer for example non small cell lung cancer. Multiple genes were interrogated to identify one or more genes having methylation of CpG islands of the genes promoter region and whose occurrence preceeded the diagnosis of cancer by months or years for example two years.

Cases from which samples were interrogated were followed over time to validate that methylation of the promoter regions of multiple genes provided a useful index as to the health of the patient and the current and future risk of developing cancer.

The method includes a nested PCR approach having a first stage PCR for amplifying the product of interest and a second stage PCR for further increasing the sensitivity for detection for the biomarker of interest. The second stage PCR includes methylation specific PCR. The second stage PCR uses primers that increase the sensitivity of detection to levels consistent with early detection. The primers and hybridization conditions provide for detection of methylated biomarkers at a sensitivity level up to 1 in 50,000. The increased sensitivity allows for detection of biomarkers predictive of lung health at about 18 months proximal to presentation of lung disease.

DEFINITIONS

As used herein, "a" means one or more unless otherwise defined.

As used herein, "algorithm" is a set of rules for describing a biological condition. The rule set may be defined exclusively algebraically but may also include alternative or multiple decision points requiring domain-specific knowledge, expert interpretation or other clinical indicators As used herein, the term "biomarker" or "marker" refers to a biological molecule, e.g., a nucleic acid, peptide, hormone, etc., whose presence or concentration can be detected and correlated with a known condition, such as a disease state. The term "biomarker" also refers to any molecule derived from a gene, e.g., a transcript of the gene or a fragment thereof, a sense (coding) or antisense (non-coding) primer sequence derived from the gene, or a full length or partial length translation product of the gene which can be used to monitor a condition, disorder, disease, or the status in the progression of a process.

As used herein, "clinical indicator" is any physiological datum used alone or in conjunction with other data in evaluating the condition of a sample or subject or of an organism. This term includes pre-clinical indicators.

As used herein, the term "a clinical sample" or "test sample" refers to a whole organism or a subset of its tissue, cells or components parts (body fluids, including but not limited to blood, mucus, lymphatic fluid, sputum). Often the sample is removed from the animal, but the term can also refer to cells or tissue, nucleic acids analyzed in vivo.

As used herein, "gene panel" is an experimentally validated set of constituents, each constituent being a distinct expressed gene wherein constituents are selected so that their measurement provides a datum for use in evaluating the health of a subject, or organism.

As used herein, "health" of a subject may include mental, emotional, physical, spiritual, allopathic, naturopathic and homeopathic condition of the subject.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids. As used herein, the term "primer" refers to a nucleic acid capable of binding to a target nucleic acid of complementary sequence through one or more types of chemical bonds, usually through complementary base pairing, usually through hydrogen bond formation. As used herein, a primer may include natural (i.e., A, G, C, or T) or modified bases (7-deazaguanosine, inosine, etc.) or sugar moiety. Further a primer is a short pre-existing polynucleotide chain to which new deoxyribonucleotides can be added by an enzyme such as a polymerase.

As used herein, the term "methylation" refers to the covalent attachment of a methyl group at the C5-position of the nucleotide base cytosine within the CpG dinucleotides of gene regulatory region. The term "hypermethylation" refers to the methylation state corresponding to an increased presence of 5-methyl-cytosine ("5-mCyt") at one or a plurality of CpG dinucleotides within a DNA sequence of a test DNA sample, relative to the amount of 5-mCyt found at corresponding CpG dinucleotides within a normal control DNA sample. The term "methylation state" or "methylation status" or "methylation level" or "the degree of methylation" refers to the presence or absence of 5-mCyt at one or a plurality of CpG dinucleotides within a DNA sequence. As used herein, the terms "methylation status" or "methylation state" or "methylation level" or "degree of methylation" are used interchangeably. A methylation site refers to a sequence of contiguous linked nucleotides that is recognized and methylated by a sequence-specific methylase. Furthermore, a methylation site also refers to a specific cytosine of a CpG dinucleotide in the CpG islands.

As used herein, "output" is defined as the promoter methylation state of any one or more genes, the combination of genes hypermethylated, the change in the number and identify of genes methylated overtime, and or other clinical indicators.

The invention is illustrated, but not limited by the following examples:

EXAMPLES

The study methodology has been described previously by Prindiville et al., in *Cancer Epidemiology Biomarkers and Prevention* 2003; 12:987-993. Potential genes useful as biomarker candidates were evaluated from the literature and from other research sources. Potential genes were validated as biomarkers after cancers were diagnosed through traditional means if the promoter region of the candidate gene was methylated prior to diagnosis.

Briefly, subjects are recruited from community and academic pulmonary clinics. At enrollment, subjects were 25 years or older with a cigarette smoking history of ≥30 pack-years, and with pulmonary air flow obstruction documented by a spirometry finding of forced expiratory volume in 1 second (FEV1) of 75% or lower than predicted for age and an FEV1/FEVC ratio of ≤0.75. Excluded were subjects who had a diagnosis of cancer within five years prior to the time of recruitment (excluding non-melanoma skin cancer), a current acute respiratory infection, or who were judged by their physician to have a life expectancy of less than 5 years. Participants were provided with two containers filled with a fixative solution of 2% carbowax and 50% alcohol (Saccommano's fixative) and instructed to collect an early morning, spontaneous cough sputum specimen for six consecutive days—three days into the first container and three into the second. Material from the second 3-day pooled sputum sample was sampled for this study.

Cohort members were contacted once a year to ask for continued participation by providing another sputum sample. Among the 3259 cohort members in this analysis there were 1353 documented deaths and 182 documented lung cancers. Cases in this analysis were those cohort members who contributed a sputum sample, who were not known or suspected to have had a cancer at enrollment and, and who were subsequently diagnosed with incident lung cancer after enrollment. Controls were cohort members matched to cases by gender, age, and month of enrollment. There were 121 cases and 120 matched controls selected for this study. Among those, DNA from 50 subjects was of insufficient quality to obtain results in the methylation-specific PCR assays. Two controls were found to be incident cases with ongoing follow-up during the course of the study. In addition, one additional case was determined to be a carcinoma in situ and was excluded. Therefore, the final analysis set included 98 cases and 92 controls.

The sputum samples were stored in Saccomanno's fixative. Four slides were prepared from sputum samples and stained using the Papanicolaou technique as described. Slides were independently screened by cytotechnologists as: not adequate for diagnosis, normal, squamous metaplasia, mild atypia, moderate atypia, severe atypia, or carcinoma. An aliquot from all sputum samples, irrespective of adequacy, for each study subject was taken and DNA was isolated by protease digestion followed by phenol chloroform extraction and ethanol precipitation. DNA (6 µg) were identified for methylation assays. Samples were labeled only with study-specific coded identifiers to blind the samples. Assays were done with both cases and controls included in each batch.

Thirty genes were selected for evaluation based on their prevalence in lung tumors (≥25%), diversity of function, timing for inactivation during lung cancer development when known, and inference of research publications. Table 7 identifies all genes interrogated for the methylation state of their promoter. Table 6 and 7 provide illustrations of, as well as the sequence of a stage 1 and stage 2 primer set for a method according to one embodiment of the present invention. The BETA3 and HLHP genes were identified through a genome wide screening approach for methylation. Candidate genes screened include laminin C2 (LAMC2), H-cadherin (HCAD), insulin-like growth factor receptor 3 (IGFBP3), BETA 3, helix-loop-helix (HLHP), secreted frizzle like protein 1 (SFRP1), RASSFIA, GATA4, GATA5, death associated protein kinase (DAPK), MGMT, PAX5-alpha, PAX-beta, p16, adenylate cyclase (AK5), adenomatous polyposis coli (APC), activator protein 2 (AP2-alpha), decoy receptor 1 (DCR1), decoy receptor 2 (DCR2), protocadherin 10 (PCDH10), progesterone (PGR), tumor suppressor gene lost in cancer (TSLC1), X transporter protein 3 (XT3), heparin sulfate D-glucosaminyl-3-O-sulfotransferase-2 (3-OST-2), differentially expressed in adenocarcinoma of the lung 1 (DAL-1), disabled homolog 2 (DAB2), FOXA2, RASSF2A, Reprimo, Tubb4 and Novel 2.

Nested methylation-specific PCR (MSP) as described in US patent application 20040038245 was used to detect methylated alleles in DNA recovered from the sputum samples. The US published application 20040038245 is incorporated herein by reference. A nested MSP assay provides for increased sensitivity for the detection of promoter hypermethylation in biological fluids. In order to conserve DNA and effort, stage 1 multiplex PCR reactions amplifying multiple genes at once was performed. For example 4 genes were amplified. DNA (120-150 ng) was used for stage 1 PCR following modification with bisulfite. PCR primers for stage 1 and 2 amplification of the p16, MGMT, DAPK, RASSF1A, PAX5-alpha and PAX5-beta genes are as described by Pamisano et al., Cancer Research 2000; 60:5954-5958, Belinsky et al., Cancer Research 2002, 62:2370-2377 and Palmisano et al., Cancer Research 2003; 63:4620-4625 and incorporated herein by reference. PCR primers used for amplification of the GATA4, GATA5, SFRP1, LAMC2, IGFBP3, BETA-3, and HLHD genes are disclosed herein. Conditions for all stage 1 multiplexes were optimized through primer design and PCR conditions to achieve equal product intensity. This ensured a similar sensitivity for the detection of methylated alleles across genes in the stage 2 MSP assay.

All stage 2 PCR reactions were conducted at annealing temperatures ranging from about 66-70° C. and that exceed the melting temperature of the second stage primers by 4-10° C. to ensure the highest specificity for amplification of methylated alleles present in the DNA sample. Cell lines positive and negative for methylation of these 30 genes and water blanks (bisulfite-modified and unmodified water) were used as controls for the MSP assays.

Because inflammatory, epithelial, and oral cells from the entire aerodigestive tract comprise the sputum sample, the contribution of DNA from epithelial cells from the lower respiratory tract can be very modest. In some situations this low abundance of DNA can have an impact on sampling for the detection of a rare methylation event, because of the exfoliation of a minimal number of epithelial cells harboring a methylation change, or the presence of a much higher number of inflammatory cells.

To address the issue of stochastic sampling for this study and its effects on sensitivity of the MSP assay, mixing experiments were conducted between cell lines positive and negative for methylation of the p16 gene. DNA isolated from Calu6 cells (p16 methylated) was added to DNA isolated from H2009 (p16 unmethylated) at dilutions ranging from 1:10 to 1:50,000. Bisulfite modification (1 μg) was performed on each sample and stage 1 MSP was conducted in triplicate, thereby sampling the modified DNA three times. Stage 2 MSP for p16 was conducted on each sample. Methylation of the p16 gene was always detected in samples containing 1:10 to 1:10,000 methylated alleles. In contrast, methylation was detected in 2 of 3 samples containing 1:20,000 and 1 of 3 samples containing 1:50,000 methylated alleles (not shown). Based on these results, we decided to assay each sputum sample in duplicate beginning with the bisulfite modification step.

Two separate aliquots (1 μg each) of DNA from each sputum sample were modified by bisulfite and subjected to MSP analysis for the 14 genes. A sample was called positive for methylation of a specific gene if either of the MSP assays were positive. The concordance between duplicate assays ranged from 65-95% for the 14 genes evaluated. As expected, the concordance between duplicate assays was inversely related to the prevalence for gene methylation in the sputum samples. A subset of samples (20%) that gave positive methylation products also was analyzed by methylation-sensitive restriction enzyme digestion of the resulting PCR product. The restriction digestion allows one to examine the methylation-state of CpGs within the amplified PCR product and serves as a control for false priming. Digestion within at least one of the restriction sites was seen for all samples positively confirming methylation.

The data was summarized using frequencies and percents fort categorical variables. Differences in distribution between cases and controls were first examined with Chi-square. Logistic regression models were then examined to assess the association between moderate atypia or worse and other risk factors. First, univariate models were examined, then multivariate models were developed that adjusted for the most important covariates. Because the matching broke down with the exclusion of some of the cases and controls, unconditional methods for multivariate analysis were used while retaining all matching variables in the models as covariates. Age was considered as a continuous variable in the analyses. Former smokers were defined as those individuals who had quit smoking 1 year or more at the time of questionnaire completion. Pack-years of cigarette smoking at enrollment was defined as the average number of packs smoked per day multiplied by the number of years of smoking. FEV-1 was the value assessed at the time of cohort enrollment. Associations were expressed as odds ratios and their corresponding 95% confidence intervals.

Analyses were conducted to assess the association with lung cancer for each gene separately, then for different combinations of genes together. Multiplicity of methylated genes was determined as the number of genes methylated in the sample collected closest to lung cancer diagnosis among a panel. For example six genes with the highest individual odds ratio are identified from table 2 which identifies the prevalence and odds for gene promoter methylation and cytological atypia in proximal sputum samples are p16, PAX5-beta, MGMT, DAPK, GATA5, and RASSF1A. The analyses was also stratified by the length of time between the sputum collection and lung cancer diagnosis (more than 18 months versus within 18 months of diagnosis). The relationship between cytological atypia and methylation was assessed, and also between methylation and the histologic type of lung cancer. Statistical significance was expressed by p values and 95% confidence intervals. However, because these were exploratory analyses, the type 1 error rate for some of the associations may be underestimated by the p values and 95% confidence intervals expressed in the tables, especially in the analysis of multiplicity among the genes in panels constructed based on the strength of association with lung cancer. All analyses were carried out using Statistical Analysis Software (SAS, version 8.1, SAS Institute, Inc., Cary, N.C.).

Selected demographic variables by case control status are summarized in Table 1 which provides a summary of selected variable by case-control status. The only significant difference seen was a greater proportion of former smokers among controls than cases. Less than two sputum samples were available for evaluation from each case and control (Table 1). Due to this limitation, the results presented are for the sputum sample collected proximal to lung cancer diagnosis for the incident cases and controls. Sputum adequacy defined as the presence of deep lung macrophages or Curschmann's spiral was observed for 93% of the proximal sputums collected from cases and controls. Persons with sputum inadequacy were mostly former smokers. Moderate or severe atypia was present in sputum from 35 and 10 subjects, respectively. The distribution of tumor histology among the 98 cases was 20% squamous cell carcinoma, 28% adenocarcinoma, 7% large cell, 8% small cell, and 37% carcinoma (subtype not specified).

TABLE 1

| Variable | Cases (n = 98) | Controls (n = 92) | P-value |
|---|---|---|---|
| | Number (%) | | |
| Age (Years) | | | 0.083 |
| 30-59 | 22 (22) | 15 (16) | |
| 60-69 | 37 (38) | 41 (45) | |
| 70+ | 39 (40) | 36 (39) | |
| Sex | | | 0.81 |
| Male | 76 (78) | 70 (76) | |
| Female | 22 (22) | 22 (24) | |
| Smoking status | | | 0.03 |
| Current | 42 (43) | 26 (28) | |
| Former | 56 (57) | 66 (72) | |
| Pack years | | | 0.24 |
| ≤50 | 32 (33) | 35 (38) | |
| 51-74 | 25 (26) | 30 (33) | |
| >75 | 41 (42) | 27 (29) | |
| Average # of sputum | 1.6 | 1.7 | 0.38 |

Samples

A standard stage 1 multiplex for amplification of the p16, MGMT, DAPK, and RASSF1A genes and a stage 2 PCR for detection of a methylated p16 gene is illustrated in FIG. 1. Referring now to FIG. 1, a gel displaying DNA from sputum samples is illustrated. Nested, MSP for amplification of the p16, MGMT, DAPK, and RASSF1A genes from sputum samples and cell lines Calu 6 and H2009 are amplified and displayed. Stage 1 products of equivalent intensity are seen for all sputum samples, Calu 6, and H2009 in panel A. The p16 gene is deleted in the MCF-7, and NIH 1435 cell lines, thus, only three PCR products are seen. The stage 1 product is diluted 1:50 and 5 μl used in a stage 2 amplification with primers specific to methylated p16. Methylation of p16 is detected in 5 sputum samples (lanes 3,4,10,14,18) and in the Calu 6 cell line. The individual odds ratio in the proximal sputum sample ranged from 0.7 to 1.9 for detecting methylation of a specific gene in cases versus controls after adjustment for age, sex, FEV1, pack years, and current smoking status (Table 2) Symbols used within the table include "*" indicating moderate atypia or worse and "†" indicating adjusted for age, sex, FEV1, pack years, and current smoking status.

The strongest association was seen for the p16 gene. In addition, the detection of cytological atypia (moderate or severe atypia) was associated with a 1.7-fold increased risk for lung cancer. Because the proximal sputum was collected from 15% and 25% of cases>2 and 4 years (up to 72 months), respectively prior to cancer diagnosis, we evaluated whether the prevalence for methylation of these biomarkers increased in the months leading up to lung cancer diagnosis.

TABLE 2

| Biomarker | Cases (%) (n = 98) | Controls (%) (n = 92) | Odds Ratio (CI) | Adjusted Odds Ratio †(CI) |
|---|---|---|---|---|
| P16 | 39 (40) | 25 (27) | 1.8 (1.0, 3.3) | 1.9 (1.0, 3.7) |
| PAX5-beta | 41 (42) | 32 (35) | 1.3 (0.7, 2.4) | 1.4 (0.7, 2.5) |
| PAX5-alpha | 28 (29) | 24 (26) | 1.1 (0.6, 2.1) | 1.2 (0.6, 2.3) |
| MGMT | 23 (24) | 22 (24) | 1.0 (0.5, 1.9) | 0.9 (0.5, 1.8) |
| DAPK | 42 (43) | 30 (33) | 1.6 (0.9, 2.8) | 1.5 (0.8, 2.7) |
| GATA5 | 34 (35) | 26 (28) | 1.3 (0.7, 2.5) | 1.4 (0.7, 2.7) |
| GATA4 | 48 (49) | 42 (46) | 1.1 (0.6, 2.0) | 1.2 (0.6, 2.1) |
| RASSF1A | 12 (12) | 6 (7) | 2.0 (0.7, 5.6) | 1.6 (0.6, 4.7) |
| SFRP1 | 68 (69) | 71 (77) | 0.7 (0.4, 1.3) | 0.7 (0.4, 1.4) |
| HLHP | 42 (43) | 36 (39) | 1.2 (0.7, 2.1) | 1.2 (0.6, 2.1) |
| BETA3 | 12 (12) | 11 (12) | 1.1 (0.5, 2.8) | 1.5 (0.6, 2.1) |
| IGFBP3 | 25 (26) | 30 (33) | 0.7 (0.4, 1.3) | 0.7 (0.3, 1.3) |
| HCAD | 27 (28) | 23 (25) | 1.1 (0.6, 2.2) | 1.2 (0.6, 2.4) |
| LAMC2 | 72 (74) | 70 (76) | 0.9 (0.5, 1.7) | 1.0 (0.5, 2.0) |
| Atypia* | 27 (28) | 12 (20) | 1.6 (0.8, 31) | 1.7 (0.9, 3.1) |

Table 3 illustrates a prevalence and odds for gene promoter methylation and cytological atypia in proximal sputum samples obtained 3-18 and 19-72 months prior to cancer diagnosis. An increase in odds for methylation was seen for the p16, PAX5-beta, MGMT, DAPK, RASSF1A, GATA4, and GATA5 genes in cases compared to controls when comparing methylation within sputum samples collected within 18 months to after 18 months. The odds ratio for cytological atypia also increased from 0.9 to 2.0. Symbols within the table are as follows: "*" indicates moderate atypia or worse. "†", indicates cases (n=52) and controls (n=47) comprised the study group for sputum samples collected within 18 months of cancer diagnosis. Cases (n=46) and controls (n=45) comprised the study group for sputum samples collected more than 18 months prior to cancer diagnosis, and "‡" indicates adjusted for age, sex, FEV1, pack years, and current smoking status.

TABLE 3

| Biomarker | Cases (%)† | Controls (%)† | Odds Ratio (CI) | Adjusted Odds Ratio‡ (CI) |
|---|---|---|---|---|
| 3-18 Months Prior to Cancer Diagnosis | | | | |
| P16 | 22 (42) | 13 (29) | 1.8 (0.9, 4.5) | 2.2 (0.9, 5.2) |
| PAX5-beta | 24 (46) | 16 (34) | 1.7 (0.7, 3.7) | 1.9 (0.8, 4.3) |
| MGMT | 17 (33) | 10 (21) | 1.8 (0.7, 1.9) | 1.7 (0.7, 4.5) |
| DAPK | 24 (46) | 16 (34) | 1.7 (0.7, 3.7) | 1.6 (0.7, 3.7) |
| GATA5 | 18 (35) | 12 (26) | 1.5 (0.6, 3.7) | 1.9 (0.7, 5.1) |
| GATA4 | 26 (50) | 20 (43) | 1.4 (0.6, 3.0) | 1.5 (0.6, 3.6) |
| RASSF1A | 7 (14) | 3 (6) | 2.3 (0.6, 9.4) | 1.7 (0.4, 7.6) |
| Atypia* | 19 (37) | 10 (21) | 2.1 (0.9, 5.2) | 2.0 (0.8, 5.2) |
| 19-72 Months Prior to Cancer Diagnosis | | | | |
| P16 | 17 (37) | 12 (27) | 1.6 (0.7, 3.9) | 1.8 (0.7, 5.0) |
| PAX5-beta | 17 (37) | 16 (36) | 1.1 (0.5, 2.5) | 1.0 (0.4, 2.6) |

TABLE 3-continued

| Biomarker | Cases (%)[†] | Controls (%)[†] | Odds Ratio (CI) | Adjusted Odds Ratio[‡] (CI) |
|---|---|---|---|---|
| MGMT | 6 (13) | 12 (27) | 0.4 (0.1, 1.2) | 0.4 (0.1, 1.3) |
| DAPK | 18 (39) | 14 (31) | 1.4 (0.6, 3.4) | 1.3 (0.5, 3.1) |
| GATA5 | 16 (35) | 14 (31) | 1.2 (0.5, 2.8) | 1.3 (0.5, 3.1) |
| GATA4 | 22 (48) | 22 (49) | 1.0 (0.4, 2.2) | 1.0 (0.4, 2.5) |
| RASSF1A | 5 (11) | 3 (7) | 1.7 (0.4, 7.6) | 1.2 (0.3, 6.0) |
| Atypia* | 8 (17) | 8 (18) | 1.0 (0.3, 2.9) | 0.9 (0.3, 2.9) |

The relationships between gene specific promoter methylation in sputum and tumor histology and cytology were examined for the p16, MGMT, PAX5-alpha, PAX-beta, DAPK, GATA4, GATA5, and RASSF1A genes. These genes were selected because they exhibit the largest increase in odds ratio when examining all proximal sputums or specimens collected within 18 months (Tables 2 and 3). There was no different pattern of methylation for the specific histologic types of lung cancer (not shown). Only the prevalence for methylation of the MGMT gene was associated with increasing cytology (moderate atypia, severe dysplasia; p value for trend=0.0393). Finally, the presence of cytological atypia in sputum samples did not predict for specific tumor histology (not shown).

The development of a gene panel for early detection of lung cancer included assessing the prevalence for detection of multiple gene methylations in individual sputum specimens. One panel of genes selected for analysis included p16, MGMT, DAPK, RASSF1A, PAX-beta, and GATA5. These genes are selected because their individual odds ratio was >1.5 in proximal sputum samples collected within 18 months of lung cancer diagnosis (Table 3). Cases with methylation of 3 or more genes in their sputum that was collected within 18 months of diagnosis had a 6.5-fold increased risk for lung cancer (95% CI, 1.2-35.5) after adjustment for age, gender, predicted FEV1, pack years and current smoking status (Table 4). This represents a sensitivity and specificity for predicting lung cancer of 64%. The addition of cytology as a biomarker to the methylation panel did not increase sensitivity or specificity for lung cancer detection (not shown).

For sputum samples collected more than 18 months before cancer diagnosis, only a 1.5-fold greater odds for methylation of 3 or more genes was seen in cases compared to controls (Table 4). Table 4 illustrates the prevalence and odds for multiple gene promoter methylation events in proximal sputum samples obtained 3-18 and 19-72 months prior to cancer diagnosis. *The genes examined include p16, MGMT, PAX-beta, DAPK, GATA5, and RASSF1A. The symbols used in Table 4 are as follows: "[†]"Cases (n=52) and controls (n=47) comprised the study group for sputum samples collected within 18 months of cancer diagnosis. Cases (n=46) and controls (n=45) comprised the study group for sputum samples collected more than 18 months prior to cancer diagnosis, and "[‡]" indicates that the data is adjusted for age, sex, FEV1, pack years, and current smoking status. The methylation state of an additional 16 genes listed in Table 5 were determined in proximal sputum samples from cases (n=54) diagnosed 3-24 months following sputum collection and the matched controls (n=47). Table 5 illustrates the prevalence and odds for gene promoter methylation in proximal sputum samples obtained 3-24 months prior to cancer diagnosis.

TABLE 4

| # Genes Methylated* | Cases (%)[†] | Controls (%)[†] | Odds Ratio (CI) | Adjusted Odds Ratio[‡] (CI) |
|---|---|---|---|---|
| 3-18 Months Prior to Cancer Diagnosis | | | | |
| 0 | 3 (6) | 7 (15) | Reference | Reference |
| 1 | 7 (14) | 13 (47) | 1.3 (0.2, 6.4) | 3.5 (0.3, 40.8) |
| 2 | 9 (17) | 10 (21) | 2.1 (0.4, 10.7) | 4.3 (0.5, 36.7) |
| ≥3 | 33 (64) | 17 (36) | 4.5 (1.0, 19.8) | 6.5 (1.2, 35.5) |
| p for trend | | | 0.004 | 0.02 |
| 19-72 Months Prior to Cancer Diagnosis | | | | |
| 0 | 7 (15) | 8 (18) | Reference | Reference |
| 1 | 7 (15) | 9 (20) | 0.9 (0.2, 3.7) | 0.5 (0.1, 2.8) |
| 2 | 13 (28) | 11 (24) | 1.4 (0.4, 4.9) | 1.5 (0.3, 6.4) |
| ≥3 | 19 (41) | 17 (38) | 1.3 (0.4, 4.3) | 1.5 (0.4, 6.3) |
| p for trend | | | 0.56 | 0.42 |

Results indicate that three genes, DAL-1 (differentially expressed in adenocarcinoma of the lung 1), DAB2 (disabled homolog 2), and RASSF2A showed 1.7 to 3.5-fold increased odds for methylation in sputum from persons who developed lung cancer compared to cancer-free controls (Table 5).

TABLE 5

| Biomarker[1] | Cases (%) | Controls (%) | Odds ratio (CI) |
|---|---|---|---|
| AK5 | 0 (0) | 2 (4.3) | — |
| APC | 22 (41) | 26 (55.3) | 0.52 (0.2, 1.2) |
| AP2-alpha | 24 (44.4) | 24 (51.0)₁ | 0.93 (0.4, 2.2) |
| DAB2 | 10 (18.5) | 4 (8.5) | 2.0 (0.4, 2.2) |
| DAL-1 | 15 (27.8) | 5 (10.6) | 3.5 (1.1, 11.5) |
| DCR1 | 24 (51.1) | 24 (51.1) | 0.9 (0.4, 2.0) |
| DCR2 | 14 (25.9) | 8 (17.0) | 1.2 (0.4, 3.6) |
| FOXA2 | 34 (63.0) | 34 (72.3) | 0.7 (0.3, 1.8) |
| PCDH10 | 19 (35.2) | 16 (34.0) | 1.3 (0.5, 3.1) |
| PGR | 28 (51.9) | 26 (55.3) | 0.9 (0.4, 2.1) |
| RASSF2A | 8 (14.8) | 4 (8.5) | 1.7 (0.5, 6.3) |
| Reprimo | 0 (0) | 2 (4.3) | — |
| TSLC1 | 2 (3.7) | 4 (8.5) | 0.8 (0.1, 5.3) |
| Tubb4 | 0 (0) | 1 (2.1) | — |
| XT3 | 2 (3.7) | 1 (2.1) | 2.3 (0.2, 28.5) |
| 3-OST-2 | 31 (57.4) | 33 (70.2) | 0.7, (0.3, 1.7) |

The odds for methylation of DAL-1, DAB2, and RASSF2A also increased when we restricted the time of the proximal sputum collected to within 18 months of clinical diagnosis. This finding is similar to previous results with the original 6-gene panel. The addition of these three genes may increase the sensitivity and specificity of the panel.

Additionally, analyzing the methylation state of the genes of interest in a second at risk population was conducted that represents the typical chronic smoker whose annual incidence of lung cancer is expected to be 0.1-0.3% compared to the 1-2% incidence seen in another cohort. Methylation is examined in sputum obtained from persons at the time of diagnosis of Stage I lung cancer. Stage I lung cancer is the type that can be removed by surgery and for which the longest survival benefit is seen. Thus, this population is ideal for initiating studies to validate a panel of genes for detection of early lung cancer.

Figure 2:
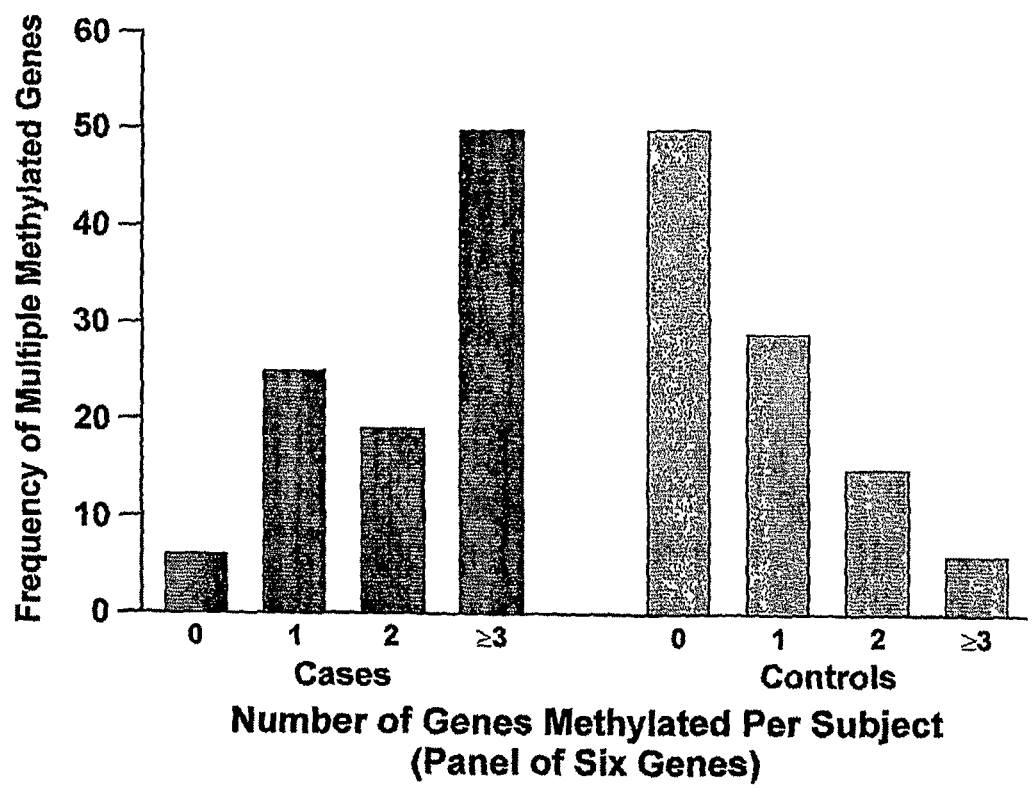
FIG. 2 illustrates the number of methylated genes in sputum from Stage I lung cancer cases compared to controls. The six genes in the panel tested were p16, MGMT, RASSF1A, DAPK, PAX5-beta and GATA5.

The prevalence for methylation of 6 genes comprising the panel p16, MGMT, RASSF1A, DAPK, PAX5-beta, and GATA5 and two other genes, GATA4 and PAX5-alpha that had displayed weaker associated for methylation in sputum from cases compared to controls were examined. Methylation for each gene was determined in sputum collected from 14 Stage I lung cancer cases (the number currently available) and 279 controls. Referring now to FIG. 2, the number of genes methylated using p16, MGMT, RASSF1A, DAPK, PAX5-beta, and GATA5 revealed that 3 or more of the 6 genes were methylated in 50% of cases and only 7% of controls. This equates to a sensitivity and specificity of 50 and 93%, respectively.

Figure 3:
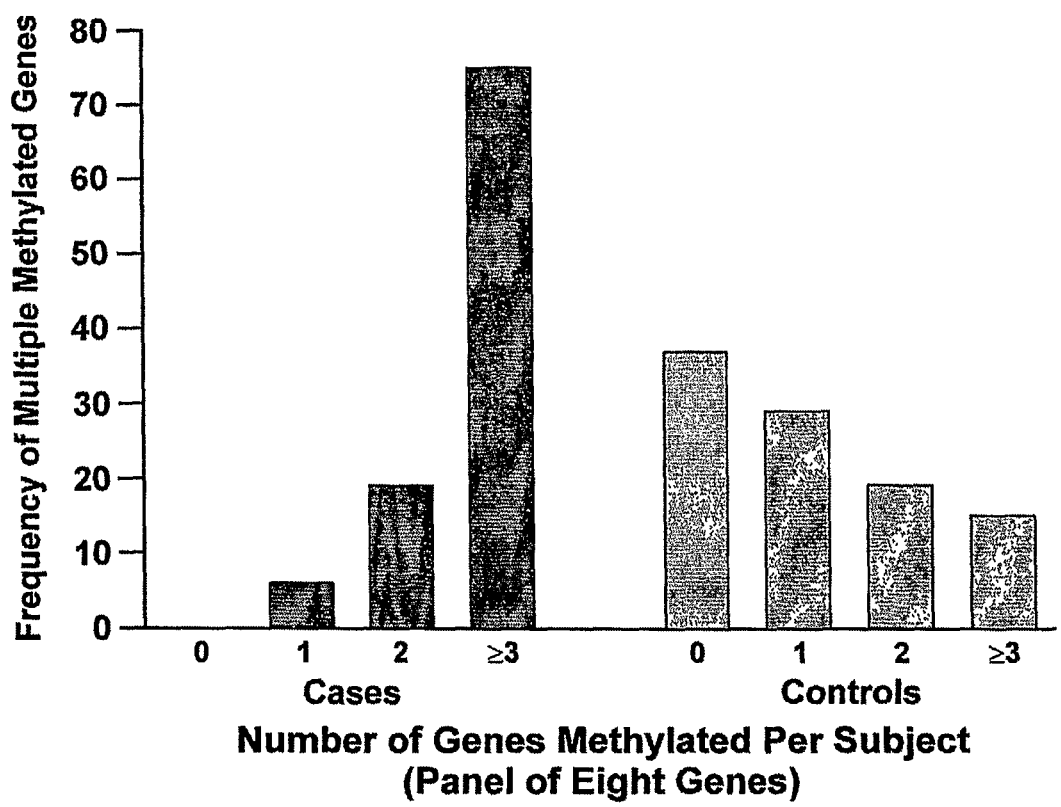
FIG. 3 illustrates number of methylated genes in sputum from Stage I lung cancer cases compared to controls. The eight genes tested in the panel were p16, MGMT, RASSF1A, DAPK, PAX5-beta, GATA5, PAX5-alpha, and GATA4.

Referring now to FIG. 3, when GATA4 and PAX5-alpha were added to the panel, 75% of cases were methylated in their sputum for 3 or more of the 8 genes, while this number of genes methylated was observed in only 15% of controls. This equates to a sensitivity of 75% and a specificity of 85% for predicting lung cancer. Together, these ongoing studies support a strategy for early detection that will interrogate a panel of 6-9 genes for methylation in sputum.

According to another embodiment of the present invention, an algorithm assigns an index to the number of genes methylated from the panel interrogated and provides an index as an indication for the subject's predisposition for developing cancer. In a preferred embodiment, the algorithm is informed by the presence or absence of other clinical indicators that are risk factors for developing cancer. For example, when there are three (3) or greater genes from the panel that are methylated in the promoter region, the index would provide an indication of a predisposition for developing cancer. When there are six (6) or more genes from the panel that are methylated in the promoter region, the index would provide a stronger indication of a predisposition for developing cancer. In addition, other clinical risk factors may be added to the algorithm such as the presence of chronic airway obstruction, family history of lung cancer, other exposures such as asbestos or number of cigarettes smoked over the person's life time. These risk factors may be used to help refine the algorithm.

Primers for stage one PCR are presented in Table 6. R and Y represent any purine or pyrimidine at that position. The temperature of annealing and duration and the melting temperature for each primer set are indicated for each gene. Each primer set contains a forward and reverse primer.

TABLE 6

| Gene | |
|---|---|
| 3-OST-2 | forward:<br>5'GTT YGG TAT TTT TYG AAG AGT TAG AT3'<br>(SEQ ID NO: 1)<br>reverse:<br>5'TTC CAA CAT CTC CCR ATC CTA AAC3'<br>(SEQ ID NO: 2)<br>annealing at 60° C. for 30 sec and a melting temperature of 70° C. |
| AK5 | forward:<br>GAG GGG TAT GAT TAY GAT TTT TTG C<br>(SEQ ID NO: 5)<br>reverse:<br>AAC CAA AAA CCC CCT CCR CCT C<br>(SEQ ID NO: 6)<br>annealing at 60° C. for 30 sec and a melting temperature of 70° C. |
| AP2-alpha also known as AP2 | forward:<br>TTT ATT TAG AGA GTA GTT TTA TTT GGG<br>(SEQ ID NO: 9)<br>reverse:<br>AAA AAT CAA ACT CRA AAC CTA TAA CC<br>(SEQ ID NO: 10)<br>annealing at 60° C. for 30 sec and a melting temperature of 68° C. |

TABLE 6-continued

| Gene | |
|---|---|
| APC | forward:<br>GGG GTT AGG GTT AGG TAG GTT GT<br>(SEQ ID NO: 13)<br>reverse:<br>AAT AAC ACC CTA ACR AAC TAC ACC A<br>(SEQ ID NO: 14)<br>annealing at 60° C. for 30 sec and a melting temperature of 70° C. |
| Beta3 | forward:<br>AAA GAA AGA AGG GGA GAG GGT TTT<br>(SEQ ID NO: 17)<br>reverse:<br>ACA ACA ACA ACC CTA CCC CCT C<br>(SEQ ID NO: 18)<br>annealing at 60° C. for 30 sec and a melting temperature of 70° C. |
| DAB2 | forward:<br>GTA TTA AGA GTT AGT TTA AGT TGG ATC<br>(SEQ ID NO: 21)<br>reverse:<br>TCT CCT CTC TTC TAC TCA CCT AAC<br>(SEQ ID NO: 22)<br>annealing at 60° C. for 30 sec and a melting temperature of 70° C. |
| DAL-1 | forward:<br>GGG YGT TAT GTT TTA AGT TGT TTT TC<br>(SEQ ID NO: 25)<br>reverse:<br>CCC CTA CCC AAC RAA AAT ACT TTA T<br>(SEQ ID NO: 26)<br>annealing at 60° C. for 30 sec and a melting temperature of 70° C. |
| DAPK | forward:<br>GGT TGT TTY GGA GTG TGA GGA GG<br>(SEQ ID NO: 53)<br>reverse:<br>CTA AAA ACT CCC CCR ATC CCT<br>(SEQ ID NO: 54)<br>annealing at 60° C. for 30 sec and a melting temperature of 70° C. |
| DCR1 | forward:<br>GAT TAG AGA TGT AAG GGG TGA AGG<br>(SEQ ID NO: 29)<br>reverse:<br>CAA ATA ACC AAA ACC AAA CAT CCC TA<br>(SEQ ID NO: 30)<br>annealing at 60° C. for 30 sec and a melting temperature of 70° C. |
| DCR2 | forward:<br>TTA TTT TGG TAG TGT AGT TGY GAG AA<br>(SEQ ID NO: 33)<br>reverse:<br>AAA TAC RCT CTT CCC CAA CCA AAA A<br>(SEQ ID NO: 34)<br>annealing at 60° C. for 30 sec and a melting temperature of 70° C. |
| FOXA2 | forward:<br>GAT TTG TYG GGT ATT GAG GTT GGA<br>(SEQ ID NO: 37)<br>reverse:<br>ATT TAA ATA ATC AAC TCA CAC CTA AAT AA<br>(SEQ ID NO: 38)<br>annealing at 60° C. for 60 sec and a melting temperature of 70° C. |

TABLE 6-continued

| Gene | |
|---|---|
| GATA4Exon 1A | forward:<br>TTA GAG TTT GGA TTT TGT TTG TTG GG<br>(SEQ ID NO: 41)<br>reverse:<br>CCC TAA AAA CCC CCR AAA CTA CAA C<br>(SEQ ID NO: 42)<br>annealing at 64° C. for 60 sec and a melting temperature of 70° C. |
| GATA5 | forward:<br>GTT TTT ATG AAA GTY GGT TTT TTG TAT<br>(SEQ ID NO: 45)<br>reverse:<br>CRT AAC CCT AAC AAA CCC TAC TC<br>(SEQ ID NO: 46)<br>annealing at 64° C. for 60 sec and a melting temperature of 70° C. |
| HCADHERIN | forward:<br>TTT TTA YGG AAA ATA TGT TTT AGT GTA GT<br>(SEQ ID NO: 49)<br>reverse:<br>TAA ACT CRA AAT AAC CTC CCT ACC<br>(SEQ ID NO: 50)<br>annealing at 64° C. for 60 sec and a melting temperature of 70° C. |
| HLHP | forward:<br>GAG GGA GAG GAG GTG GGA GAG<br>(SEQ ID NO: 57)<br>reverse:<br>CRT AAC CRT AAC TTA ATA CCA AAT AC<br>(SEQ ID NO: 58)<br>annealing at 62° C. for 60 sec and a melting temperature of 70° C. |
| PAX5-alpha | forward:<br>GGG TTT GTA TAT GGA GAT GTT ATA G<br>(SEQ ID NO: 61)<br>reverse:<br>CAA CAT CAC AAA ATA TCC CCA AAC AC<br>(SEQ ID NO: 62)<br>annealing at 64° C. for 60 sec and a melting temperature of 70° C. |
| PAX5-beta | forward:<br>AGT TTG TGG GTT GTT TAG TTA ATG G<br>(SEQ ID NO: 65)<br>reverse:<br>CAA AAA ATC CCA ACC ACC AAA ACC<br>(SEQ ID NO: 66)<br>annealing at 64° C. for 60 sec and a melting temperature of 70° C. |
| RASSF1A | forward:<br>GGA GGG AAG GAA GGG TAA GG<br>(SEQ ID NO: 69)<br>reverse:<br>CAA CTC AAT AAA CTC AAA CTC CC<br>(SEQ ID NO: 70)<br>annealing at 60° C. for 60 sec and a melting temperature of 64° C. |
| RASSF2A | forward:<br>GTA GGG GTT GAA AAA GGT TAA GGG<br>(SEQ ID NO: 73)<br>reverse:<br>CCA ATA CCT CRC TCC CAA TAC C<br>(SEQ ID NO: 74)<br>annealing at 60° C. for 30 sec and a melting temperature of 70° C. |

TABLE 6-continued

| Gene | |
|---|---|
| IGFBP3 | forward:<br>TGT TTT GGG TTA TTT YGG TTT TTA TAT A<br>(SEQ ID NO: 77)<br>reverse:<br>CAC CAC YAA ACC CAA ACC CCC C<br>(SEQ ID NO: 78)<br>annealing at 62° C. for 60 sec and a melting temperature of 70° C. |
| LAMC2 | forward:<br>GGG AAT TTY GTA TAT TTT AGG TAA AGG<br>(SEQ ID NO: 81)<br>reverse:<br>CTC ACC TTC CCT CCT AAA AAT AAC C<br>(SEQ ID NO: 82)<br>annealing at 62° C. for 60 sec and a melting temperature of 72° C. |
| MGMT | forward:<br>GTT TYG GAT ATG TTG GGA TAG TT<br>(SEQ ID NO: 85)<br>reverse:<br>AAC ACT AAA ACR CCA CCT AAA ACT C<br>(SEQ ID NO: 86)<br>annealing at 60° C. for 30 sec and a melting temperature of 70° C. |
| Novel 2 | forward:<br>GGT TTA GTT YGG AGG AAG GAT TTT TA<br>(SEQ ID NO: 89)<br>reverse:<br>TAA TAA TAA TCC AAA TAC RCC AAA CC<br>(SEQ ID NO: 90)<br>annealing at 62° C. for 60 sec and a melting temperature of 68° C. |
| P16 | forward:<br>GAG GAA GAA AGA GGA GGG GTT G<br>(SEQ ID NO: 93)<br>reverse:<br>ACA AAC CCT CTA CCC ACC TAA ATC<br>(SEQ ID NO: 94)<br>annealing at 60° C. for 30 sec and a melting temperature of 70° C. |
| PCDH10 | forward:<br>TTG YGG TTG GGG ATT GGG AAT TTT<br>(SEQ ID NO: 97)<br>reverse:<br>TAT AAT CTA AAC TAA CAA TTT CTA AAC TC<br>(SEQ ID NO: 98)<br>annealing at 60° C. for 60 sec and a melting temperature of 70° C. |
| PGR | forward:<br>GGG ATT TGA GAT TTT YGG AGA TGA T<br>(SEQ ID NO: 101)<br>reverse:<br>AAA TTC TCC AAC TTC TAT CCR AAA AC<br>(SEQ ID NO: 102)<br>annealing at 60° C. for 30 sec and a melting temperature of 70° C. |
| Reprimo | forward:<br>AGA GGT TTT TGG GAA ATT TTT AYG GT<br>(SEQ ID NO: 105)<br>reverse:<br>GAT CTA CAC CAC RCA CAT TAT ATA C<br>(SEQ ID NO: 106)<br>annealing at 60° C. for 30 sec and a melting temperature of 70° C. |
| SFRP1 | forward:<br>TAG TTT TGT AGT TTT YGG AGT TAG TGT<br>(SEQ ID NO: 109)<br>reverse: |

TABLE 6-continued

| Gene | |
|---|---|
| | CAA ACT ACT ACC CYA TCC CCC C<br>(SEQ ID NO: 110)<br>annealing at 62° C. for 60 sec and a<br>melting temperature of 70° C. |
| TSLC1 | forward:<br>GGG AAA GTA AAA TTY GAA TTT TAA TAT A<br>(SEQ ID NO: 113)<br>reverse:<br>TAT CRA ACA CCT ACC TCA AAC TAA C<br>(SEQ ID NO: 114)<br>annealing at 60° C. for 30 sec and a<br>melting temperature of 68° C. |
| TUBB4 | forward:<br>TAT TAT TTY GGG GYG GGA TTA AGG<br>(SEQ ID NO: 117)<br>reverse:<br>ATT CCT TTC CAA AAA CTC CCA AAT TA<br>(SEQ ID NO: 118)<br>annealing at 60° C. for 30 sec and a<br>melting temperature of 70° C. |
| XT3 | forward:<br>GAG TYG GAG GAT TTT AGG GGA TT<br>(SEQ ID NO: 121)<br>reverse:<br>GCT TTC TCC ATA ACC CCR ACC T<br>(SEQ ID NO: 122)<br>annealing at 60° C. for 30 sec and a<br>melting temperature of 68° C. |

Table 7 illustrates the second stage primer set for each gene interrogated. The temperature of annealing and duration and the melting temperature of each primer set is provided. The temperature of annealing for the second stage primer is above the melting temperature of the second stage primer, for example, by 4-10° C. Preferably the annealing temperature is about 4-8° C. above the melting temperature of the second stage primer.

TABLE 7

| Gene | |
|---|---|
| 3-OST-2 | forward:<br>CGG CGT TAG CGT TAT CGT TC<br>(SEQ ID NO: 3)<br>reverse:<br>AAA CTC CGA ACA ACC GAA CG<br>(SEQ ID NO: 4)<br>Annealing at 68° C. for 20 sec and a<br>melting temperature of 60° C. |
| AK5 | forward:<br>AGT CGT CGT AGA TTC GGT TC<br>(SEQ ID NO: 7)<br>reverse:<br>AAC CGA AAC TAC AAA CGC CG<br>(SEQ ID NO: 8)<br>Annealing at 68° C. for 15 sec and a<br>melting temperature of 60° C. |
| AP2-alpha also known as AP2 | forward:<br>AGG GGT ATA TTC GTT TAC GTC<br>(SEQ ID NO: 11)<br>reverse:<br>GCA CGA ATA ATC AAA CCG ACG<br>(SEQ ID NO: 12)<br>Annealing at 68° C. for 15 sec and a<br>melting temperature of 60° C. |

TABLE 7-continued

| Gene | |
|---|---|
| APC | forward:<br>TTA TTG CGG AGT GCG GGT C<br>(SEQ ID NO: 15)<br>reverse:<br>CCA CAT ATC GAT CAC GTA CG<br>(SEQ ID NO: 16)<br>Annealing at 68° C. for 15 sec and a<br>melting temperature of 60° C. |
| Beta3 | forward:<br>CGG AGT TTA GTT CGC GCG C<br>(SEQ ID NO: 19)<br>reverse:<br>GAA CGT TCC CGA AAC GAC G<br>(SEQ ID NO: 20)<br>Annealing at 68° C. for 20 Sec and a<br>melting temperature of 60° C. |
| DAB2 | forward:<br>TTC GGA GCG TCG TCG TCG<br>(SEQ ID NO: 23)<br>reverse:<br>TAA ATT CCC GAC GAA CGA CG<br>(SEQ ID NO: 24)<br>Annealing at 68° C. for 20 sec and a<br>melting temperature of 60° C. |
| DAL-1 | forward:<br>GGC GAG CGC GGG TCG G<br>(SEQ ID NO: 27)<br>reverse:<br>CCC CGC GCT ACG CCC G<br>(SEQ ID NO: 28)<br>annealing at 68° C. for 20 sec and a<br>melting temperature of 60° C. |
| DAPK | forward:<br>ATA GTC GGA TCG AGT TAA CGT C<br>(SEQ ID NO: 55)<br>reverse:<br>AAA ACT AAC CGA AAC GAC GAC G<br>(SEQ ID NO: 56)<br>annealing at 70° C. for 15 sec and a<br>melting temperature of 64° C. |
| DCR1 | forward:<br>GTT TCG GTC GTT TGA TGG TC<br>(SEQ ID NO: 31)<br>reverse:<br>CCT CCC GAC GCC AAA TAC G<br>(SEQ ID NO: 32)<br>annealing at 68° C. for 20 sec and a<br>melting temperature of 60° C. |
| DCR2 | forward:<br>CGC GTA TAA ATT ACG GGG AC<br>(SEQ ID NO: 35)<br>reverse:<br>CCG CGA CGA TAA AAA CGA CG<br>(SEQ ID NO: 36)<br>annealing at 68° C. for 15 sec and a<br>melting temperature of 60° C. |
| FOXA2 | forward:<br>GCG TAT CGG GCG TTC GGC<br>(SEQ ID NO: 39)<br>reverse:<br>ACG AAC GAT CGA ACA CGC G<br>(SEQ ID NO: 40)<br>annealing at 66° C. for 20 sec and a<br>melting temperature of 62° C. |

TABLE 7-continued

| Gene | |
|---|---|
| GATA4Exon 1A | forward:<br>GAG GTG TAG TCG GGG TCG C<br>(SEQ ID NO: 43)<br>reverse:<br>GCG ACC CCT ACG CCG ACC G<br>(SEQ ID NO: 44)<br>annealing at 70° C. for 20 sec and a melting temperature of 60° C. |
| GATA5 | forward:<br>TTA CGG GGT TTT ATC GTC GC<br>(SEQ ID NO: 47)<br>reverse:<br>TAC AAC TAA ACG AAC GAA CCG<br>(SEQ ID NO: 48)<br>annealing at 66° C. for 20 sec and a melting temperature of 60° C. |
| HCADHERIN | forward:<br>GAA TGA AAA CGT CGT CGG GC<br>(SEQ ID NO: 51)<br>reverse:<br>ATC TAT CTT CGC CGC CGC G<br>(SEQ ID NO: 52)<br>annealing at 70° C. for 15 sec and a melting temperature of 62° C. |
| HLHP | forward:<br>GAG GAG GTA GCG GGC GTC<br>(SEQ ID NO: 59)<br>reverse:<br>TCG ACC ATA ACC GCG CCG<br>(SEQ ID NO: 60)<br>annealing at 68° C. for 20 sec and a melting temperature of 64° C. |
| PAX5-alpha | forward:<br>ATA AAA GTT TGG GGC GGC GC<br>(SEQ ID NO: 63)<br>reverse:<br>GCG CCC CCA ACG CGC CG<br>(SEQ ID NO: 64)<br>annealing at 66° C. for 15 sec and a melting temperature of 60° C. |
| PAX5-beta | forward:<br>GAG TTG AGT TTC GGG CGG C<br>(SEQ ID NO: 67)<br>reverse:<br>GCC GCC GCC GCC GTC G<br>(SEQ ID NO: 68)<br>annealing at 68° C. for 15 sec and a melting temperature of 62° C. |
| RASSF1A | forward:<br>GGG GGT TTT GCG AGA GCG C<br>(SEQ ID NO: 71)<br>reverse:<br>CCC GAT TAA ACC CGT ACT TCG<br>(SEQ ID NO: 72)<br>annealing at 68° C. for 20 sec and a melting temperature of 60° C. |
| RASSF2A | forward:<br>CGT TCG GTT TTT AGT CGC GC<br>(SEQ ID NO: 75)<br>reverse:<br>GCG CCC CGC GCC CCG<br>(SEQ ID NO: 76)<br>annealing at 68° C. for 15 sec and a melting temperature of 62° C. |
| IGFBP3 | forward:<br>GGT CGG CGC GTT CGG GTC<br>(SEQ ID NO: 79)<br>reverse:<br>CAA AAC GTA AAT CGC GCC CG<br>(SEQ ID NO: 80)<br>annealing at 68° C. for 15 sec and a melting temperature of 62° C. |
| LAMC2 | forward:<br>GGT GTG CGT TTT TTT CGT TGC<br>(SEQ ID NO: 83)<br>reverse:<br>TAC AAA AAT CGC TAC CCG ACG<br>(SEQ ID NO: 84)<br>annealing at 68° C. for 20 sec and a melting temperature of 62° C. |
| MGMT | forward:<br>ACG TTT TGC GTT TCG ACG TTC<br>(SEQ ID NO: 87)<br>reverse:<br>ACC CCC CAC CCG ACG ACG<br>(SEQ ID NO: 88)<br>annealing at 68° C. for 15 sec and a melting temperature of 64° C. |
| Novel 2 | forward:<br>GGT CGG AAT AAT AGC GCG C<br>(SEQ ID NO: 91)<br>reverse:<br>GAA CGT CCA TAA CGA ACG CG<br>(SEQ ID NO: 92)<br>annealing at 68° C. for 20 sec and a melting temperature of 60° C. |
| P16 | forward:<br>GAG GGT GGG GCG GAT CGC<br>(SEQ ID NO: 95)<br>reverse:<br>GAC CCC GAA CCG CGA CCG<br>(SEQ ID NO: 96)<br>annealing at 70° C. for 15 sec and a melting temperature of 64° C. |
| PCDH10 | forward:<br>ATT TAT TTT GGT CGT TCG GGC<br>(SEQ ID NO: 99)<br>reverse:<br>CGA ACG CTC GAC TTC TCC G<br>(SEQ ID NO: 100)<br>annealing at 66° C. for 20 sec and a melting temperature of 60° C. |
| PGR | forward:<br>GAT GAT TGT CGT TCG TAG TAC<br>(SEQ ID NO: 102)<br>reverse:<br>GCG ACT CCT TTA TCT CCC G<br>(SEQ ID NO: 103)<br>annealing at 68° C. for 20 sec and a melting temperature of 60° C. |
| Reprimo | forward:<br>CGA GGA GTT TTC GTA CGC G<br>(SEQ ID NO: 107)<br>reverse:<br>ACA AAC CCG CCA CGT CCG<br>(SEQ ID NO: 108)<br>annealing at 68° C. for 20 sec and a melting temperature of 60° C. |

TABLE 7-continued

| Gene | |
|---|---|
| SFRP1 | forward:<br>CGC GCG TTC GTC GTT TCG C<br>(SEQ ID NO: 109)<br>reverse:<br>AAT AAC GAC CCT CGA CCT ACG<br>(SEQ ID NO: 110)<br>annealing at 68° C. for 20 sec and a melting temperature of 64° C. |
| TSLC1 | forward:<br>GTG GCG CGG GCG CGT C<br>(SEQ ID NO: 113)<br>reverse:<br>TAC CTC CGA AAC CCG AAC G<br>(SEQ ID NO: 114)<br>annealing at 69° C. for 20 sec and a melting temperature of 60° C. |
| TUBB4 | forward:<br>CGT GTT TCG TCG TTT TCG TC<br>(SEQ ID NO: 117)<br>reverse:<br>CCG AAC CCC GTT CCC CG<br>(SEQ ID NO: 118)<br>annealing at 69° C. for 20 sec and a melting temperature of 60° C. |
| XT3 | forward:<br>CGG TTG CGA CGA TCG GGC<br>(SEQ ID NO: 121)<br>reverse:<br>CGA CTC GAA AAT CCG ACA CG<br>(SEQ ID NO: 122)<br>annealing at 68° C. for 15 sec and a melting temperature of 60° C. |

Another embodiment of the present invention comprises a computer program product for enabling a computer to produce an index value correlating to the health of a subject from one or more clinical indicators. The computer program product includes software instructions for enabling the computer to perform predetermined operations, and a computer readable medium embodying the software instructions. The pre-determined operations include identifying the methylation state of a promoter of one or more genes from a panel comprising p16, MGMT, DAPK, PAX5-alpha, PAX5-beta, RASSF1A, DAB-2, DAL-1, RASSF2A, GATA5, and GATA4 to determine a number of genes having hypermethylation of the promoter; applying an algorithm to the number of genes having hypermethylation of the promoter to produce an index value correlating to the health of a subject. The operation may automatically identify the promoter regions of the genes that are hypermethylated from a gel or other experimental data or may accept user input data identifying the genes having hypermethylation in their promoter region. The algorithm may also weigh the presence of chronic airway obstruction, family history of lung cancer, exposure to asbestos or number of cigarettes smoked over the person's life time to produce an index value correlating to the health of the patient.

According to another embodiment of the present invention, a computer system is adopted to correlate the health of a subject from clinical indicators and includes a processor and a memory including software instructions adapted to enable the computer system to perform operations comprising: identifying the methylation state of a promoter of one or more genes from a panel comprising p16, MGMT, DAPK, PAX5-alpha, PAX5-beta, RASSF1A, DAB-2, DAL-1, RASSF2A, GATA5, and GATA4 to determine the number of genes having hypermethylation of the promoter; applying an algorithm to the number of genes having hypermethylation of the promoter to produce an index value correlating to the health of a subject.

Although the present invention has been described in terms of specific embodiments, various substitutions of materials and conditions can be made as will be known to those skilled in the art. For example, the primer sets may be modified without changing the scope of the invention. Other variations will be apparent to those skilled in the art and are meant to be included herein. The scope of the invention is only to be limited by the following claims.

What is claimed is:

1. A method to identify a subject at increased risk for developing lung cancer or suspected of having lung cancer prior to the clinical diagnosis of lung cancer comprising:
obtaining a test sample selected from sputum containing DNA from the subject wherein the subject is a current or former smoker;
subjecting the DNA to bisulfite modification;
expanding the number of copies of a portion of each gene selected from p16, MGMT, DAPK, PAX5-alpha, PAX5-beta, RASSF1A, DAL-1, and GATA5 by using a polymerase chain reaction with a multiplex of four primer pairs wherein each of a primer pair of the primer pairs anneals to a different gene from the plurality of genes at a length of DNA within the promoter region having a bisulfite modified cytosine to amplify the portion where a promoter methylation resides, thereby generating an amplification product;
in a second, methylation-specific, polymerase chain reaction using an aliquot of the amplification product with a methylation-specific primer pair specific for one gene from the plurality of genes amplified in the amplification product wherein the methylation specific primer anneals where the promoter methylation resides and wherein the methylation-specific primer pair has a temperature of annealing that exceeds the melting temperature of the second primer set; and
detecting the presence of methylation in six or more genes in a test sample of the subject not previously diagnosed with lung cancer wherein the six or more genes are selected from p16, MGMT, DAPK, PAX5-alpha, PAX5-beta, RASSF1A, DAL-1, and GATA5 wherein methylation in the promoter region of six or more genes selected from p16, MGMT, DAPK, PAX5-alpha, PAX5-beta, RASSF1A, DAL-1 and GATA5 identifies the current or former smoker subject as at increased risk of developing lung cancer or suspected of having lung cancer as compared to the current or former smoker subject without methylation in the promoter region of the six or more genes wherein the multiplex of primer pairs in the expanding step are selected from the primer pairs consisting of: (SEQ ID NO 93, SEQ ID NO: 94); (SEQ ID NO: 85, SEQ ID NO: 86); (SEQ ID NO: 53, SEQ ID NO: 54); (SEQ ID NO: 61, SEQ ID NO: 62); (SEQ ID NO: 65, SEQ ID NO: 66); (SEQ ID NO: 69, SEQ ID NO: 70); (SEQ ID NO: 25, SEQ ID NO: 26); and (SEQ ID NO: 45, SEQ ID NO: 46).

2. The method of claim 1 further comprising applying an algorithm to the presence of methylation of the portion of each gene to produce an index value correlating to the increased risk for developing lung cancer or suspected of having lung cancer.

3. The method of claim 2 wherein the index value correlating to the increased risk for developing lung cancer or suspected of having lung cancer produced by the algorithm is further informed by clinical indicators selected from one or more of the following: the presence of chronic airway obstruction, family history of lung cancer, exposure to asbestos or number of cigarettes smoked over the subject's life time.

4. The method of claim 1 wherein a portion of a 274 base pair fragment of the p16 gene is interrogated with a methylation-specific primer set comprising:

```
Forward                              (SEQ ID NO: 95)
5' GAG GGT GGG GCG GAT CGC 3'

Reverse                              (SEQ ID NO: 96)
5' GAC CCC GAA CCG CGA CCG 3'.
```

5. The method of claim 1 wherein a portion of a 251 base pair fragment of the MGMT gene is interrogated with a methylation-specific primer set comprising:

```
Forward                              (SEQ ID NO: 87)
5' ACG TTT TGC GTT TCG ACG TTC 3'

Reverse:                             (SEQ ID NO: 88)
5' ACC CCC CAC CCG ACG ACG 3'.
```

6. The method of claim 1 wherein a portion of a 236 base pair fragment of the DAPK gene is interrogated with a methylation-specific primer set comprising:

```
Forward                              (SEQ ID NO: 55)
5' ATA GTC GGA TCG AGT TAA CGT C 3'

Reverse:                             (SEQ ID NO: 56)
5' AAA ACT AAC CGA AAC GAC GAC G 3'.
```

7. The method of claim 1 wherein a portion of a 388 base pair fragment of the PAX5-alpha gene is interrogated with a methylation-specific primer set comprising:

```
Forward                              (SEQ ID NO: 63)
5' ATA AAA GTT TGG GGC GGC GC 3'

Reverse:                             (SEQ ID NO: 64)
5' GCG CCC CCA ACG CGC CG 3'.
```

8. The method of claim 1 wherein a portion of a 318 base pair fragment of the PAX5-beta gene is interrogated with a methylation-specific primer set comprising:

```
Forward                              (SEQ ID NO: 67)
5' GAG TTG AGT TTC GGG CGG C 3'

Reverse:                             (SEQ ID NO: 68)
5' GCC GCC GCC GCC GTC G 3'.
```

9. The method of claim 1 wherein a portion of a 260 base pair fragment of the RASSF1A gene is interrogated with a methylation-specific primer set comprising:

```
Forward                              (SEQ ID NO: 71)
5' GGG GGT TTT GCG AGA GCG C 3'

Reverse:                             (SEQ ID NO: 72)
5' CCC GAT TAA ACC CGT ACT TCG 3'.
```

10. The method of claim 1 wherein a portion of a 247 base pair fragment of the DAL-1 gene is interrogated with a methylation-specific primer set comprising:

```
Forward                              (SEQ ID NO: 27)
5' GGC GAG CGC GGG TCG G 3'

Reverse:                             (SEQ ID NO: 28)
5' CCC CGC GCT ACG CCC G 3'.
```

11. The method of claim 1 wherein a portion of a 348 base pair fragment of the GATA5 gene is interrogated with a methylation-specific primer set comprising:

```
Forward                              (SEQ ID NO: 47)
5' TTA CGG GGT TTT ATC GTC GC 3'

Reverse:                             (SEQ ID NO: 48)
5' TAC AAC TAA ACG AAC GAA CCG 3'.
```

12. The method of claim 1 wherein the multiplex of four primer pairs are specific for p16 (SEQ ID NO 93-94), MGMT(SEQ ID NO 85-86), DAPK(SEQ ID NO 53-54) and RASSF1A(SEQ ID NO 69-70).

13. A method of monitoring the efficacy of therapy for treating lung cancer in a subject in need thereof comprising:
obtaining a first test sample selected from sputum containing DNA from the subject at a first time point;
subjecting the DNA to bisulfite modification;
providing a multiplex of primer pairs wherein each of a primer pair of the multiplex of the primer pairs hybridizes to a complimentary CpG promoter region from each of the genes selected from the group consisting of p16, MGMT, DAPK, PAX5-alpha, PAX5-beta, RASSF1A, DAL-1, and GATA5;
contacting the multiplex of primer pairs with the first test sample;
analyzing DNA from the first test sample for a methylation of the promoter region for each of p16, MGMT, DAPK, PAX5-alpha, PAX5-beta, RASSF1A, DAL-1, and GATA5;
providing the therapy for treating lung cancer to the subject;
after providing the therapy, obtaining a second test sample selected from sputum containing DNA from the subject at a second time point;
subjecting the DNA from the second test sample to bisulfite modification;
providing a multiplex of primer pairs wherein each of a primer pair of the multiplex of primer pairs hybridizes to a CpG promoter region of a different gene from the plurality of genes selected from the group consisting of p16, MGMT, DAPK, PAX5-alpha, PAX5-beta, RASSF1A, DAL-1, and GATA5;
contacting the multiplex of primer pairs with the second test sample; and
analyzing DNA from the first test sample and the second test sample for a change in methylation of the promoter region for each of p16, MGMT, DAPK, PAX5-alpha, PAX5-beta, RASSF1A, DAL-1, and GATA5 and comparing the methylation state of the promoter region for each of p16, MGMT, DAPK, PAX5-alpha, PAX5-beta, RASSF1A, DAL-1, and GATA5 before the therapy to the methylation state of the promoter region for each of p16, MGMT, DAPK, PAX5-alpha, PAX5-beta, RASSF1A, DAL-1, and GATA5 after therapy to monitor the efficacy of the therapy for treating lung cancer in a subject wherein a decrease in the methylation state of the promoter region of the second test sample indicates efficacy of the therapy wherein the multiplex of primer pairs in the contacting step are selected from the primer pairs consisting of: (SEQ ID NO 93, SEQ ID NO: 94); (SEQ ID NO: 85, SEQ ID NO: 86); (SEQ ID NO: 53, SEQ ID NO: 54); (SEQ ID NO: 61, SEQ ID NO: 62); (SEQ ID NO: 65, SEQ ID NO: 66); (SEQ ID NO: 69, SEQ ID NO: 70); (SEQ ID NO: 25, SEQ ID NO: 26); and (SEQ ID NO: 45, SEQ ID NO: 46).

14. A method to identify a subject at increased risk for developing lung cancer or suspected of having lung cancer prior to the clinical diagnosis of lung cancer comprising:
obtaining a test sample selected from sputum containing DNA from the subject wherein the subject is a current or former smoker;
subjecting the DNA to bisulfite modification;
expanding the number of copies of each gene selected from p16, MGMT, DAPK, PAX5-alpha, PAX5-beta, RASSF1A, DAL-1, and GATA5 by using a polymerase chain reaction with a multiplex of four primer pairs to amplify a portion of the selected gene where the promoter methylation resides, thereby generating an amplification product wherein the multiplex of four primer pairs comprises SEQ ID NO: 45-46 or SEQ ID NO: 25-26;

in a methylation-specific polymerase chain reaction, using an aliquot of the amplification product with a methylation-specific primer pair having a temperature of annealing that exceeds the melting temperature of the methylation-specific primer set; and detecting the presence of methylation of each gene in a subject not previously diagnosed with lung cancer wherein each gene is selected from p16, MGMT, DAPK, PAX5-alpha, PAX5-beta, RASSF1A, DAL-1, and GATA5 wherein methylation in the promoter region of six or more genes selected from p16, MGMT, DAPK, PAX5-alpha, PAX5-beta, RASSF1A, DAL-1 and GATA5 identifies the current or former smoker subject as at increased risk of developing lung cancer or suspected of having lung cancer as compared to the current or former smoker subject without methylation in the promoter region of six or more genes selected from p16, MGMT, DAPK, PAX5-alpha, PAX5-beta, RASSF1A, DAL-1 and GATA5.

\* \* \* \* \*

SEQUENCE LISTING

```
<160> NUMBER OF SEQ ID NOS: 124

<210> SEQ ID NO 1
<211> LENGTH: 26
<212> TYPE: DNA
<213> ORGANISM: Homo sapiens

<400> SEQUENCE: 1
gttyggtatt tttygaagag ttagat                                      26

<210> SEQ ID NO 2
<211> LENGTH: 24
<212> TYPE: DNA
<213> ORGANISM: Homo sapiens

<400> SEQUENCE: 2
ttccaacatc tcccratcct aaac                                        24

<210> SEQ ID NO 3
<211> LENGTH: 20
<212> TYPE: DNA
<213> ORGANISM: Homo sapiens
```

```
<400> SEQUENCE: 3
cggcgttagc gttatcgttc                                              20

<210> SEQ ID NO 4
<211> LENGTH: 20
<212> TYPE: DNA
<213> ORGANISM: Homo sapiens

<400> SEQUENCE: 4
aaactccgaa caaccgaacg                                              20

<210> SEQ ID NO 5
<211> LENGTH: 25
<212> TYPE: DNA
<213> ORGANISM: Homo sapiens

<400> SEQUENCE: 5
gaggggtatg attaygattt tttgc                                        25

<210> SEQ ID NO 6
<211> LENGTH: 22
<212> TYPE: DNA
<213> ORGANISM: Homo sapiens

<400> SEQUENCE: 6
aaccaaaaac ccctccrcc tc                                            22

<210> SEQ ID NO 7
<211> LENGTH: 20
<212> TYPE: DNA
<213> ORGANISM: Homo sapiens

<400> SEQUENCE: 7
agtcgtcgta gattcggttc                                              20

<210> SEQ ID NO 8
<211> LENGTH: 20
<212> TYPE: DNA
<213> ORGANISM: Homo sapiens

<400> SEQUENCE: 8
aaccgaaact acaaacgccg                                              20

<210> SEQ ID NO 9
<211> LENGTH: 27
<212> TYPE: DNA
<213> ORGANISM: Homo sapiens

<400> SEQUENCE: 9
tttatttaga gagtagtttt atttggg                                      27

<210> SEQ ID NO 10
<211> LENGTH: 26
<212> TYPE: DNA
<213> ORGANISM: Homo sapiens

<400> SEQUENCE: 10
aaaaatcaaa ctcraaacct ataacc                                       26

<210> SEQ ID NO 11
<211> LENGTH: 21
<212> TYPE: DNA
<213> ORGANISM: Homo sapiens
```

```
<400> SEQUENCE: 11
aggggtatat tcgtttacgt c                                              21

<210> SEQ ID NO 12
<211> LENGTH: 21
<212> TYPE: DNA
<213> ORGANISM: Homo sapiens

<400> SEQUENCE: 12
gcacgaataa tcaaaccgac g                                              21

<210> SEQ ID NO 13
<211> LENGTH: 23
<212> TYPE: DNA
<213> ORGANISM: Homo sapiens

<400> SEQUENCE: 13
ggggttaggg ttaggtaggt tgt                                            23

<210> SEQ ID NO 14
<211> LENGTH: 25
<212> TYPE: DNA
<213> ORGANISM: Homo sapiens

<400> SEQUENCE: 14
aataacaccc taacraacta cacca                                          25

<210> SEQ ID NO 15
<211> LENGTH: 19
<212> TYPE: DNA
<213> ORGANISM: Homo sapiens

<400> SEQUENCE: 15
ttattgcgga gtgcgggtc                                                 19

<210> SEQ ID NO 16
<211> LENGTH: 20
<212> TYPE: DNA
<213> ORGANISM: Homo sapiens

<400> SEQUENCE: 16
ccacatatcg atcacgtacg                                                20

<210> SEQ ID NO 17
<211> LENGTH: 24
<212> TYPE: DNA
<213> ORGANISM: Homo sapiens

<400> SEQUENCE: 17
aaagaaagaa ggggagaggg tttt                                           24

<210> SEQ ID NO 18
<211> LENGTH: 22
<212> TYPE: DNA
<213> ORGANISM: Homo sapiens

<400> SEQUENCE: 18
acaacaacaa ccctaccccc tc                                             22

<210> SEQ ID NO 19
<211> LENGTH: 19
<212> TYPE: DNA
```

<213> ORGANISM: Homo sapiens

<400> SEQUENCE: 19
cggagtttag ttcgcgcgc                                                19

<210> SEQ ID NO 20
<211> LENGTH: 19
<212> TYPE: DNA
<213> ORGANISM: Homo sapiens

<400> SEQUENCE: 20
gaacgttccc gaaacgacg                                                19

<210> SEQ ID NO 21
<211> LENGTH: 27
<212> TYPE: DNA
<213> ORGANISM: Homo sapiens

<400> SEQUENCE: 21
gtattaagag ttagtttaag ttggatc                                       27

<210> SEQ ID NO 22
<211> LENGTH: 24
<212> TYPE: DNA
<213> ORGANISM: Homo sapiens

<400> SEQUENCE: 22
tctcctctct tctactcacc taac                                          24

<210> SEQ ID NO 23
<211> LENGTH: 18
<212> TYPE: DNA
<213> ORGANISM: Homo sapiens

<400> SEQUENCE: 23
ttcggagcgt cgtcgtcg                                                 18

<210> SEQ ID NO 24
<211> LENGTH: 20
<212> TYPE: DNA
<213> ORGANISM: Homo sapiens

<400> SEQUENCE: 24
taaattcccg acgaacgacg                                               20

<210> SEQ ID NO 25
<211> LENGTH: 26
<212> TYPE: DNA
<213> ORGANISM: Homo sapiens

<400> SEQUENCE: 25
gggygttatg ttttaagttg tttttc                                        26

<210> SEQ ID NO 26
<211> LENGTH: 25
<212> TYPE: DNA
<213> ORGANISM: Homo sapiens

<400> SEQUENCE: 26
cccctaccca acraaaatac tttat                                         25

<210> SEQ ID NO 27
<211> LENGTH: 16

```
<212> TYPE: DNA
<213> ORGANISM: Homo sapiens

<400> SEQUENCE: 27
ggcgagcgcg ggtcgg                                                   16

<210> SEQ ID NO 28
<211> LENGTH: 16
<212> TYPE: DNA
<213> ORGANISM: Homo sapiens

<400> SEQUENCE: 28
ccccgcgcta cgcccg                                                   16

<210> SEQ ID NO 29
<211> LENGTH: 24
<212> TYPE: DNA
<213> ORGANISM: Homo sapiens

<400> SEQUENCE: 29
gattagagat gtaagggtg aagg                                           24

<210> SEQ ID NO 30
<211> LENGTH: 26
<212> TYPE: DNA
<213> ORGANISM: Homo sapiens

<400> SEQUENCE: 30
caaataacca aaaccaaaca tcccta                                        26

<210> SEQ ID NO 31
<211> LENGTH: 20
<212> TYPE: DNA
<213> ORGANISM: Homo sapiens

<400> SEQUENCE: 31
gtttcggtcg tttgatggtc                                               20

<210> SEQ ID NO 32
<211> LENGTH: 19
<212> TYPE: DNA
<213> ORGANISM: Homo sapiens

<400> SEQUENCE: 32
cctcccgacg ccaaatacg                                                19

<210> SEQ ID NO 33
<211> LENGTH: 26
<212> TYPE: DNA
<213> ORGANISM: Homo sapiens

<400> SEQUENCE: 33
ttattttggt agtgtagttg ygagaa                                        26

<210> SEQ ID NO 34
<211> LENGTH: 25
<212> TYPE: DNA
<213> ORGANISM: Homo sapiens

<400> SEQUENCE: 34
aaatacrctc ttccccaacc aaaaa                                         25

<210> SEQ ID NO 35
```

-continued

```
<211> LENGTH: 20
<212> TYPE: DNA
<213> ORGANISM: Homo sapiens

<400> SEQUENCE: 35
cgcgtataaa ttacggggac                                              20

<210> SEQ ID NO 36
<211> LENGTH: 20
<212> TYPE: DNA
<213> ORGANISM: Homo sapiens

<400> SEQUENCE: 36
ccgcgacgat aaaaacgacg                                              20

<210> SEQ ID NO 37
<211> LENGTH: 24
<212> TYPE: DNA
<213> ORGANISM: Homo sapiens

<400> SEQUENCE: 37
gatttgtygg gtattgaggt tgga                                         24

<210> SEQ ID NO 38
<211> LENGTH: 29
<212> TYPE: DNA
<213> ORGANISM: Homo sapiens

<400> SEQUENCE: 38
atttaaataa tcaactcaca cctaaataa                                    29

<210> SEQ ID NO 39
<211> LENGTH: 18
<212> TYPE: DNA
<213> ORGANISM: Homo sapiens

<400> SEQUENCE: 39
gcgtatcggg cgttcggc                                                18

<210> SEQ ID NO 40
<211> LENGTH: 19
<212> TYPE: DNA
<213> ORGANISM: Homo sapiens

<400> SEQUENCE: 40
acgaacgatc gaacacgcg                                               19

<210> SEQ ID NO 41
<211> LENGTH: 26
<212> TYPE: DNA
<213> ORGANISM: Homo sapiens

<400> SEQUENCE: 41
ttagagtttg gattttgttt gttggg                                       26

<210> SEQ ID NO 42
<211> LENGTH: 25
<212> TYPE: DNA
<213> ORGANISM: Homo sapiens

<400> SEQUENCE: 42
ccctaaaaac cccraaact acaac                                         25
```

<210> SEQ ID NO 43
<211> LENGTH: 19
<212> TYPE: DNA
<213> ORGANISM: Homo sapiens

<400> SEQUENCE: 43
gaggtgtagt cggggtcgc                                               19

<210> SEQ ID NO 44
<211> LENGTH: 19
<212> TYPE: DNA
<213> ORGANISM: Homo sapiens

<400> SEQUENCE: 44 gcgacccta cgccgaccg                                                19

<210> SEQ ID NO 45
<211> LENGTH: 27
<212> TYPE: DNA
<213> ORGANISM: Homo sapiens

<400> SEQUENCE: 45
gtttttatgg aagtyggttt tttgtat                                      27

<210> SEQ ID NO 46
<211> LENGTH: 23
<212> TYPE: DNA
<213> ORGANISM: Homo sapiens

<400> SEQUENCE: 46
crtaacccta acaaaccta ctc                                           23

<210> SEQ ID NO 47
<211> LENGTH: 20
<212> TYPE: DNA
<213> ORGANISM: Homo sapiens

<400> SEQUENCE: 47
ttacggggtt ttatcgtcgc                                              20

<210> SEQ ID NO 48
<211> LENGTH: 21
<212> TYPE: DNA
<213> ORGANISM: Homo sapiens

<400> SEQUENCE: 48
tacaactaaa cgaacgaacc g                                            21

<210> SEQ ID NO 49
<211> LENGTH: 29
<212> TYPE: DNA
<213> ORGANISM: Homo sapiens

<400> SEQUENCE: 49
tttttaygga aaatatgttt tagtgtagt                                    29

<210> SEQ ID NO 50
<211> LENGTH: 24
<212> TYPE: DNA
<213> ORGANISM: Homo sapiens

<400> SEQUENCE: 50
taaactcraa ataacctccc tacc                                         24

<210> SEQ ID NO 51
<211> LENGTH: 20
<212> TYPE: DNA
<213> ORGANISM: Homo sapiens

<400> SEQUENCE: 51
gaatgaaaac gtcgtcgggc          20

<210> SEQ ID NO 52
<211> LENGTH: 19
<212> TYPE: DNA
<213> ORGANISM: Homo sapiens

<400> SEQUENCE: 52
atctatcttc gccgccgcg           19

<210> SEQ ID NO 53
<211> LENGTH: 23
<212> TYPE: DNA
<213> ORGANISM: Homo sapiens

<400> SEQUENCE: 53
ggttgtttyg gagtgtgagg agg      23

<210> SEQ ID NO 54
<211> LENGTH: 21
<212> TYPE: DNA
<213> ORGANISM: Homo sapiens

<400> SEQUENCE: 54
ctaaaaactc ccccratccc t        21

<210> SEQ ID NO 55
<211> LENGTH: 22
<212> TYPE: DNA
<213> ORGANISM: Homo sapiens

<400> SEQUENCE: 55
atagtcggat cgagttaacg tc       22

<210> SEQ ID NO 56
<211> LENGTH: 22
<212> TYPE: DNA
<213> ORGANISM: Homo sapiens

<400> SEQUENCE: 56
aaaactaacc gaaacgacga cg       22

<210> SEQ ID NO 57
<211> LENGTH: 21
<212> TYPE: DNA
<213> ORGANISM: Homo sapiens

<400> SEQUENCE: 57
gagggagagg aggtgggaga g        21

<210> SEQ ID NO 58
<211> LENGTH: 26
<212> TYPE: DNA
<213> ORGANISM: Homo sapiens

<400> SEQUENCE: 58
crtaaccrta acttaatacc aaatac   26

<210> SEQ ID NO 59
<211> LENGTH: 18
<212> TYPE: DNA
<213> ORGANISM: Homo sapiens

<400> SEQUENCE: 59
gaggaggtag cgggcgtc                                                      18

<210> SEQ ID NO 60
<211> LENGTH: 18
<212> TYPE: DNA
<213> ORGANISM: Homo sapiens

<400> SEQUENCE: 60
tcgaccataa ccgcgccg                                                      18

<210> SEQ ID NO 61
<211> LENGTH: 25
<212> TYPE: DNA
<213> ORGANISM: Homo sapiens

<400> SEQUENCE: 61
gggtttgtat atggagatgt tatag                                              25

<210> SEQ ID NO 62
<211> LENGTH: 26
<212> TYPE: DNA
<213> ORGANISM: Homo sapiens

<400> SEQUENCE: 62
caacatcaca aaatatcccc aaacac                                             26

<210> SEQ ID NO 63
<211> LENGTH: 20
<212> TYPE: DNA
<213> ORGANISM: Homo sapiens

<400> SEQUENCE: 63
ataaaagttt ggggcggcgc                                                    20

<210> SEQ ID NO 64
<211> LENGTH: 17
<212> TYPE: DNA
<213> ORGANISM: Homo sapiens

<400> SEQUENCE: 64
gcgcccccaa cgcgccg                                                       17

<210> SEQ ID NO 65
<211> LENGTH: 25
<212> TYPE: DNA
<213> ORGANISM: Homo sapiens

<400> SEQUENCE: 65
agtttgtggg ttgtttagtt aatgg                                              25

<210> SEQ ID NO 66
<211> LENGTH: 24
<212> TYPE: DNA
<213> ORGANISM: Homo sapiens

<400> SEQUENCE: 66
caaaaaatcc caaccaccaa aacc                                              24

<210> SEQ ID NO 67
<211> LENGTH: 19
<212> TYPE: DNA
<213> ORGANISM: Homo sapiens

<400> SEQUENCE: 67
gagttgagtt tcgggcggc                                                    19

<210> SEQ ID NO 68
<211> LENGTH: 16
<212> TYPE: DNA
<213> ORGANISM: Homo sapiens

<400> SEQUENCE: 68
gccgccgccg ccgtcg                                                       16

<210> SEQ ID NO 69
<211> LENGTH: 20
<212> TYPE: DNA
<213> ORGANISM: Homo sapiens

<400> SEQUENCE: 69
ggagggaagg aagggtaagg                                                   20

<210> SEQ ID NO 70
<211> LENGTH: 23
<212> TYPE: DNA
<213> ORGANISM: Homo sapiens

<400> SEQUENCE: 70
caactcaata aactcaaact ccc                                               23

<210> SEQ ID NO 71
<211> LENGTH: 19
<212> TYPE: DNA
<213> ORGANISM: Homo sapiens

<400> SEQUENCE: 71
gggggttttg cgagagcgc                                                    19

<210> SEQ ID NO 72
<211> LENGTH: 21
<212> TYPE: DNA
<213> ORGANISM: Homo sapiens

<400> SEQUENCE: 72
cccgattaaa cccgtacttc g                                                 21

<210> SEQ ID NO 73
<211> LENGTH: 24
<212> TYPE: DNA
<213> ORGANISM: Homo sapiens

<400> SEQUENCE: 73 gtagggttg aaaaggtta aggg                                                24

<210> SEQ ID NO 74
<211> LENGTH: 22
<212> TYPE: DNA
<213> ORGANISM: Homo sapiens

<400> SEQUENCE: 74

```
ccaataccct rctcccaata cc                                          22
```

<210> SEQ ID NO 75
<211> LENGTH: 20
<212> TYPE: DNA
<213> ORGANISM: Homo sapiens

<400> SEQUENCE: 75

```
cgttcggttt ttagtcgcgc                                             20
```

<210> SEQ ID NO 76
<211> LENGTH: 15
<212> TYPE: DNA
<213> ORGANISM: Homo sapiens

<400> SEQUENCE: 76

```
gcgccccgcg ccccg                                                  15
```

<210> SEQ ID NO 77
<211> LENGTH: 28
<212> TYPE: DNA
<213> ORGANISM: Homo sapiens

<400> SEQUENCE: 77

```
tgttttgggt tatttyggtt tttatata                                    28
```

<210> SEQ ID NO 78
<211> LENGTH: 22
<212> TYPE: DNA
<213> ORGANISM: Homo sapiens

<400> SEQUENCE: 78

```
caccacyaaa cccaaacccc cc                                          22
```

<210> SEQ ID NO 79
<211> LENGTH: 18
<212> TYPE: DNA
<213> ORGANISM: Homo sapiens

<400> SEQUENCE: 79

```
ggtcggcgcg ttcgggtc                                               18
```

<210> SEQ ID NO 80
<211> LENGTH: 20
<212> TYPE: DNA
<213> ORGANISM: Homo sapiens

<400> SEQUENCE: 80

```
caaaacgtaa atcgcgcccg                                             20
```

<210> SEQ ID NO 81
<211> LENGTH: 27
<212> TYPE: DNA
<213> ORGANISM: Homo sapiens

<400> SEQUENCE: 81

```
gggaatttyg tatattttag gtaaagg                                     27
```

<210> SEQ ID NO 82
<211> LENGTH: 25
<212> TYPE: DNA
<213> ORGANISM: Homo sapiens

<400> SEQUENCE: 82
ctcaccttcc ctcctaaaaa taacc                                              25

<210> SEQ ID NO 83
<211> LENGTH: 21
<212> TYPE: DNA
<213> ORGANISM: Homo sapiens

<400> SEQUENCE: 83
ggtgtgcgtt tttttcgttg c                                                  21

<210> SEQ ID NO 84
<211> LENGTH: 21
<212> TYPE: DNA
<213> ORGANISM: Homo sapiens

<400> SEQUENCE: 84
tacaaaaatc gctacccgac g                                                  21

<210> SEQ ID NO 85
<211> LENGTH: 23
<212> TYPE: DNA
<213> ORGANISM: Homo sapiens

<400> SEQUENCE: 85
gtttyggata tgttgggata gtt                                                23

<210> SEQ ID NO 86
<211> LENGTH: 25
<212> TYPE: DNA
<213> ORGANISM: Homo sapiens

<400> SEQUENCE: 86
aacacttaaa acrcacctaa aactc                                              25

<210> SEQ ID NO 87
<211> LENGTH: 21
<212> TYPE: DNA
<213> ORGANISM: Homo sapiens

<400> SEQUENCE: 87
acgttttgcg tttcgacgtt c                                                  21

<210> SEQ ID NO 88
<211> LENGTH: 18
<212> TYPE: DNA
<213> ORGANISM: Homo sapiens

<400> SEQUENCE: 88 acccccacc cgacgacg                                                       18

<210> SEQ ID NO 89
<211> LENGTH: 26
<212> TYPE: DNA
<213> ORGANISM: Homo sapiens

<400> SEQUENCE: 89
ggtttagtty ggaggaagga ttttta                                             26

<210> SEQ ID NO 90
<211> LENGTH: 26
<212> TYPE: DNA
<213> ORGANISM: Homo sapiens

<400> SEQUENCE: 90
taataataat ccaaatacrc caaacc                                              26

<210> SEQ ID NO 91
<211> LENGTH: 19
<212> TYPE: DNA
<213> ORGANISM: Homo sapiens

<400> SEQUENCE: 91
ggtcggaata atagcgcgc                                                      19

<210> SEQ ID NO 92
<211> LENGTH: 20
<212> TYPE: DNA
<213> ORGANISM: Homo sapiens

<400> SEQUENCE: 92
gaacgtccat aacgaacgcg                                                     20

<210> SEQ ID NO 93
<211> LENGTH: 22
<212> TYPE: DNA
<213> ORGANISM: Homo sapiens

<400> SEQUENCE: 93
gaggaagaaa gaggaggggt tg                                                  22

<210> SEQ ID NO 94
<211> LENGTH: 24
<212> TYPE: DNA
<213> ORGANISM: Homo sapiens

<400> SEQUENCE: 94
acaaaccctc tacccaccta aatc                                                24

<210> SEQ ID NO 95
<211> LENGTH: 18
<212> TYPE: DNA
<213> ORGANISM: Homo sapiens

<400> SEQUENCE: 95
gagggtgggg cggatcgc                                                       18

<210> SEQ ID NO 96
<211> LENGTH: 18
<212> TYPE: DNA
<213> ORGANISM: Homo sapiens

<400> SEQUENCE: 96
gaccccgaac cgcgaccg                                                       18

<210> SEQ ID NO 97
<211> LENGTH: 24
<212> TYPE: DNA
<213> ORGANISM: Homo sapiens

<400> SEQUENCE: 97
ttgyggttgg ggattgggaa tttt                                                24

<210> SEQ ID NO 98
<211> LENGTH: 29
<212> TYPE: DNA

```
<213> ORGANISM: Homo sapiens

<400> SEQUENCE: 98
tataatctaa actaacaatt tctaaactc                                    29

<210> SEQ ID NO 99
<211> LENGTH: 21
<212> TYPE: DNA
<213> ORGANISM: Homo sapiens

<400> SEQUENCE: 99
atttattttg gtcgttcggg c                                            21

<210> SEQ ID NO 100
<211> LENGTH: 19
<212> TYPE: DNA
<213> ORGANISM: Homo sapiens

<400> SEQUENCE: 100
cgaacgctcg acttctccg                                               19

<210> SEQ ID NO 101
<211> LENGTH: 25
<212> TYPE: DNA
<213> ORGANISM: Homo sapiens

<400> SEQUENCE: 101
gggatttgag attttyggag atgat                                        25

<210> SEQ ID NO 102
<211> LENGTH: 26
<212> TYPE: DNA
<213> ORGANISM: Homo sapiens

<400> SEQUENCE: 102
aaattctcca acttctatcc raaaac                                       26

<210> SEQ ID NO 103
<211> LENGTH: 21
<212> TYPE: DNA
<213> ORGANISM: Homo sapiens

<400> SEQUENCE: 103
gatgattgtc gttcgtagta c                                            21

<210> SEQ ID NO 104
<211> LENGTH: 19
<212> TYPE: DNA
<213> ORGANISM: Homo sapiens

<400> SEQUENCE: 104
gcgactcctt tatctcccg                                               19

<210> SEQ ID NO 105
<211> LENGTH: 26
<212> TYPE: DNA
<213> ORGANISM: Homo sapiens

<400> SEQUENCE: 105
agaggttttt gggaaattt tayggt                                        26

<210> SEQ ID NO 106
<211> LENGTH: 25
```

```
<212> TYPE: DNA
<213> ORGANISM: Homo sapiens

<400> SEQUENCE: 106
gatctacacc acrcacatta tatac                                          25

<210> SEQ ID NO 107
<211> LENGTH: 19
<212> TYPE: DNA
<213> ORGANISM: Homo sapiens

<400> SEQUENCE: 107
cgaggagttt tcgtacgcg                                                 19

<210> SEQ ID NO 108
<211> LENGTH: 18
<212> TYPE: DNA
<213> ORGANISM: Homo sapiens

<400> SEQUENCE: 108
acaaacccgc cacgtccg                                                  18

<210> SEQ ID NO 109
<211> LENGTH: 27
<212> TYPE: DNA
<213> ORGANISM: Homo sapiens

<400> SEQUENCE: 109
tagttttgta gttttyggag ttagtgt                                        27

<210> SEQ ID NO 110
<211> LENGTH: 22
<212> TYPE: DNA
<213> ORGANISM: Homo sapiens

<400> SEQUENCE: 110
caaactacta cccyatcccc cc                                             22

<210> SEQ ID NO 111
<211> LENGTH: 19
<212> TYPE: DNA
<213> ORGANISM: Homo sapiens

<400> SEQUENCE: 111
cgcgcgttcg tcgtttcgc                                                 19

<210> SEQ ID NO 112
<211> LENGTH: 21
<212> TYPE: DNA
<213> ORGANISM: Homo sapiens

<400> SEQUENCE: 112
aataacgacc ctcgacctac g                                              21

<210> SEQ ID NO 113
<211> LENGTH: 28
<212> TYPE: DNA
<213> ORGANISM: Homo sapiens

<400> SEQUENCE: 113
gggaaagtaa aattygaatt ttaatata                                       28

<210> SEQ ID NO 114
```

```
<211> LENGTH: 25
<212> TYPE: DNA
<213> ORGANISM: Homo sapiens

<400> SEQUENCE: 114
tatcraacac ctacctcaaa ctaac                                      25

<210> SEQ ID NO 115
<211> LENGTH: 16
<212> TYPE: DNA
<213> ORGANISM: Homo sapiens

<400> SEQUENCE: 115
gtggcgcggg cgcgtc                                                16

<210> SEQ ID NO 116
<211> LENGTH: 19
<212> TYPE: DNA
<213> ORGANISM: Homo sapiens

<400> SEQUENCE: 116
tacctccgaa acccgaacg                                             19

<210> SEQ ID NO 117
<211> LENGTH: 24
<212> TYPE: DNA
<213> ORGANISM: Homo sapiens

<400> SEQUENCE: 117
tattatttyg gggygggatt aagg                                       24

<210> SEQ ID NO 118
<211> LENGTH: 26
<212> TYPE: DNA
<213> ORGANISM: Homo sapiens

<400> SEQUENCE: 118
attcctttcc aaaaactccc aaatta                                     26

<210> SEQ ID NO 119
<211> LENGTH: 20
<212> TYPE: DNA
<213> ORGANISM: Homo sapiens

<400> SEQUENCE: 119
cgtgtttcgt cgttttcgtc                                            20

<210> SEQ ID NO 120
<211> LENGTH: 17
<212> TYPE: DNA
<213> ORGANISM: Homo sapiens

<400> SEQUENCE: 120
ccgaaccccg ttccccg                                               17

<210> SEQ ID NO 121
<211> LENGTH: 23
<212> TYPE: DNA
<213> ORGANISM: Homo sapiens

<400> SEQUENCE: 121
gagtyggagg attttagggg att                                        23
```

```
<210> SEQ ID NO 122
<211> LENGTH: 22
<212> TYPE: DNA
<213> ORGANISM: Homo sapiens

<400> SEQUENCE: 122
gctttctcca taaccccrac ct                                              22

<210> SEQ ID NO 123
<211> LENGTH: 18
<212> TYPE: DNA
<213> ORGANISM: Homo sapiens

<400> SEQUENCE: 123
cggttgcgac gatcgggc                                                   18

<210> SEQ ID NO 124
<211> LENGTH: 20
<212> TYPE: DNA
<213> ORGANISM: Homo sapiens

<400> SEQUENCE: 124
cgactcgaaa atccgacacg                                                 20
```